United States Patent
Ishihara et al.

(10) Patent No.: US 12,029,450 B2
(45) Date of Patent: Jul. 9, 2024

(54) BIODEGRADABLE MEDICAL IMPLEMENT

(71) Applicants: NITTO SEIKO CO., LTD., Ayabe (JP); KYOTO PREFECTURAL PUBLIC UNIVERSITY CORPORATION, Kyoto-shi (JP); Wook-Cheol Kim, Kyoto (JP); NATIONAL UNIVERSITY CORPORATION UNIVERSITY OF TOYAMA, Toyama (JP)

(72) Inventors: Masakazu Ishihara, Ayabe (JP); Yoshimitsu Ueno, Ayabe (JP); Tomoaki Murata, Ayabe (JP); Yukito Otsuki, Ayabe (JP); Yusuke Kobayashi, Ayabe (JP); Yoshinobu Oka, Kyoto (JP); Wook-Cheol Kim, Kyoto (JP); Tetsuo Aida, Toyama (JP); Sadami Tsutsumi, Kyoto (JP)

(73) Assignees: NITTO SEIKO CO., LTD., Kyoto (JP); KYOTO PREFECTURAL PUBLIC UNIVERSITY CORPORATION, Kyoto (JP); Wook-Cheol Kim, Kyoto (JP); NATIONAL UNIVERISTY CORPORATION UNIVERSITY OF TOYAMA, Toyama (JP); Sadami Tsutsumi, Kyoto (JP)

( * ) Notice: Subject to any disclaimer, the term of this patent is extended or adjusted under 35 U.S.C. 154(b) by 0 days.

(21) Appl. No.: 18/266,639

(22) PCT Filed: Nov. 29, 2021

(86) PCT No.: PCT/JP2021/043582
§ 371 (c)(1),
(2) Date: Jun. 12, 2023

(87) PCT Pub. No.: WO2022/130948
PCT Pub. Date: Jun. 23, 2022

(65) Prior Publication Data
US 2024/0041497 A1    Feb. 8, 2024

(30) Foreign Application Priority Data
Dec. 14, 2020    (JP) .................. 2020-207080

(51) Int. Cl.
*A61B 17/58* (2006.01)
*A61L 31/02* (2006.01)
*A61B 17/00* (2006.01)

(52) U.S. Cl.
CPC ............ *A61B 17/58* (2013.01); *A61L 31/022* (2013.01); *A61B 2017/00004* (2013.01)

(58) Field of Classification Search
CPC .............................. A61B 17/58; A61L 31/022
See application file for complete search history.

(56) References Cited

U.S. PATENT DOCUMENTS

2015/0297370 A1 * 10/2015 Hanada ................... B21B 17/04
72/283
2019/0274851 A1    9/2019 Hanada et al.

FOREIGN PATENT DOCUMENTS

| WO | 2013/021913 A1 | 2/2013 |
| WO | 2014/021454 A1 | 2/2014 |

OTHER PUBLICATIONS

International Search Report dated Jan. 25, 2022, issued in counterpart International Application No. PCT/JP2021/043582 (2 pages).
(Continued)

*Primary Examiner* — Christian A Sevilla
(74) *Attorney, Agent, or Firm* — WHDA, LLP

(57) ABSTRACT

To ensure that a biodegradable medical implement dissolves in vivo at an appropriate dissolution rate. The biodegradable medical implement of the present invention is formed of a
(Continued)

magnesium material, and, at least in one transverse section, a layer of magnesium crystal grains in which a (0001) plane in a hexagonal crystal structure is oriented toward a surface side is continuous over an entire circumference.

12 Claims, 28 Drawing Sheets

(56) References Cited

OTHER PUBLICATIONS

Notice of Reasons for Refusal dated May 30, 2023, issued in counterpart JP Patent Application No. 2022-569830, w/ English machine translation (7 pages).

* cited by examiner

TRANSVERSE SECTION
(AXIS 3 DIRECTION)

TRANSVERSE SECTION
(AXIS 1 DIRECTION)

TRANSVERSE SECTION
(AXIS 2 DIRECTION)

LONGITUDINAL SECTION
(AXIS 3 DIRECTION)

LONGITUDINAL SECTION
(AXIS 2 DIRECTION)

TRANSVERSE SECTION
(AXIS 3 DIRECTION)

TRANSVERSE SECTION
(AXIS 1 DIRECTION)

TRANSVERSE SECTION
(AXIS 2 DIRECTION)

TRANSVERSE SECTION
(AXIS 3 DIRECTION)

TRANSVERSE SECTION
(AXIS 1 DIRECTION)

TRANSVERSE SECTION
(AXIS 2 DIRECTION)

LONGITUDINAL SECTION
(AXIS 3 DIRECTION)

LONGITUDINAL SECTION
(AXIS 1 DIRECTION)

LONGITUDINAL SECTION
(AXIS 2 DIRECTION)

LONGITUDINAL SECTION
(AXIS 3 DIRECTION)

LONGITUDINAL SECTION
(AXIS 1 DIRECTION)

LONGITUDINAL SECTION
(AXIS 2 DIRECTION)

TRANSVERSE SECTION
(AXIS 1 DIRECTION)

LONGITUDINAL SECTION (AXIS 1 DIRECTION)

(SAMPLE N1)

(SAMPLE N2)

BIODEGRADABLE MEDICAL IMPLEMENT

TECHNICAL FIELD

The present invention relates to a biodegradable medical implement.

BACKGROUND ART

Conventionally, some medical implements for attaching or fixing bones are formed of metal materials. In this case, in order to prevent the metal medical implement from remaining in the body after treatment, the medical implement is usually removed by another operation after the treatment or recovery. However, since another operation puts a heavy burden on the patient, a biodegradable medical implement that dissolves in vivo has been developed. As a material for the biodegradable medical implement that dissolve in vivo, a high-purity magnesium material having appropriate strength is considered (e.g., see Patent literature 1).

PRIOR ART DOCUMENT

Patent Document

Patent Document 1: WO 2013/021913

SUMMARY OF THE INVENTION

Technical Problem

However, a problem with the high-purity magnesium material with low corrosion resistance in vivo is in that it dissolves quickly.

Solution to Problem

The inventor of the present invention has studied to control the corrosion resistance (dissolubility) of a biodegradable medical implement by changing the orientation of magnesium crystal grains.

It is known that magnesium crystal grains have a hexagonal close-packed structure, and when a (0001) plane in the structure is oriented toward a surface side of the biodegradable medical implement, the corrosion resistance of the magnesium crystal grains increases, which makes the magnesium crystal grains hardly dissolvable. Thus, the inventor of the present invention has studied how the corrosion resistance of the biodegradable medical implement changes when, with respect to the surface of the biodegradable medical, the area (an area ratio with respect to the entire surface) of a part where the (0001) plane of the magnesium crystal grains is oriented toward the surface side is changed.

As a result of intensive studies on the above, the inventor of the present invention has found that, although the corrosion resistance of the biodegradable medical implement can improve to some extent by increasing, with respect to the surface of the biodegradable medical, the area of the part where the (0001) plane of the magnesium crystal grains is oriented toward the surface side, if there is a part, on the surface of the degradable medical implement, where a (10-10) plane or a (2-1-10) plane, which has low corrosion resistance and is highly dissolvable, is oriented toward the surface side, dissolution progresses from the surface toward the center portion through such a part, thereby reducing the corrosion resistance of the biodegradable medical implement. For this reason, it has been difficult to significantly improve the corrosion resistance of the biodegradable medical implement.

Regarding this, as a result of further studies, the inventor of the present invention has found that, when, in a predetermined cross section of a biodegradable medical implement, a layer of magnesium crystal grains in which the (0001) plane in the hexagonal crystal structure is oriented toward the surface side of the implement is continuous over the entire circumference, the corrosion resistance of the biodegradable medical implement significantly improves, thereby making the biodegradable medical implement hardly dissolvable.

That is, a biodegradable medical implement according to the present invention is characterized in that the biodegradable medical implement is formed of a magnesium material, and, at least in one predetermined cross section, a layer of magnesium crystal grains in which the (0001) plane in the hexagonal crystal structure is oriented toward the surface side is continuous over the entire circumference.

Note that, in the present invention, for example, in a case where the biodegradable medical implement is a long implement, in a transverse section, the "magnesium crystal grains in which the (0001) plane in the hexagonal crystal structure is oriented toward the surface side" includes "magnesium crystal grains in which the (0001) plane in the hexagonal crystal structure is arranged perpendicular with respect to the normal direction of the implement surface" and "magnesium crystal grains in which the normal direction of the (0001) plane in the hexagonal crystal structure is inclined by 0 to 45 degrees with respect to the normal direction of the implement surface (the direction of inclination may be in any direction)". Further, in the present invention, for example, in the case where the biodegradable medical implement is a long implement, in the transverse section, the sentence "the layer of magnesium crystal grains is continuous over the entire circumference" means that "the layer of magnesium crystal grains surrounds the center portion of the biodegradable medical implement".

As a result, in the biodegradable medical implement according to the present invention, in the predetermined cross section, the layer of magnesium crystal grains in which the (0001) plane having higher corrosion resistance in vivo than the (10-10) plane and the (2-1-10) plane in the hexagonal crystal structure is oriented toward the surface side is continuous over the entire circumference. Thus, dissolution hardly progresses from the surface of the biodegradable medical implement toward the center portion of the implement from any direction in the circumferential direction. Thus, as compared with the case where the magnesium crystal grains in which the (10-10) plane or the (2-1-10) plane, which has the low corrosion resistance in vivo, is oriented toward the surface side are present at least in a part of the surface of the biodegradable medical implement, the progress of dissolution from the surface of the biodegradable medical implement toward the center portion of the implement is delayed. This can improve the corrosion resistance of the biodegradable medical implement to make the biodegradable medical implement hardly dissolvable.

In the biodegradable medical implement according to the present invention, the layer of magnesium crystal grains is characterized by being continuous in a direction perpendicular to the predetermined cross section.

Note that, in the present invention, the sentence "the layer of magnesium crystal grains is continuous in a direction perpendicular to the predetermined cross section" means that, for example, in the case where the biodegradable medical implement is a long implement, "the layer of magnesium crystal grains in which the (0001) plane in the hexagonal crystal structure is oriented toward the surface side is continuous over the entire circumference in the transverse section, and the layer of magnesium crystal grains is also continuous in the longitudinal direction". Note that the layer of magnesium crystal grains is only required to be continuous at least in a part of the elongated implement in the longitudinal direction.

As a result, in the biodegradable medical implement according to the present invention, in the predetermined cross section, the layer of magnesium crystal grains, in which the dissolution hardly progresses from the surface of the biodegradable medical implement toward the center portion of the implement from any direction in the circumferential direction, is continuous in the direction perpendicular to the predetermined cross section. Thus, the area ratio of the part where the layer of magnesium crystal grains is inside is relatively large with respect to the entire surface of the entire instrument. This can further improve the corrosion resistance of the biodegradable medical implement to make the biodegradable medical implement hardly dissolvable.

In the biodegradable medical implement according to the present invention, the magnesium material is characterized by being a pure magnesium material containing 99.9% by mass or more of magnesium.

As a result, in the biodegradable medical implement according to the present invention, even if a high-purity magnesium material having the low corrosion resistance in vivo is used as the magnesium material, it is possible to improve the corrosion resistance of the biodegradable medical implement to make the biodegradable medical implement hardly dissolvable.

In the biodegradable medical implement according to the present invention, the magnesium material is characterized by being a magnesium alloy containing magnesium as a main component.

As a result, in the biodegradable medical implement according to the present invention, even if a magnesium alloy containing magnesium as a main component is used as the magnesium material, it is possible to improve the corrosion resistance of the biodegradable medical implement to make the biodegradable medical implement hardly dissolvable.

Advantageous Effect of the Invention

As described above, according to the present invention, the corrosion resistance (dissolubility) of the biodegradable medical implement is controlled so that the biodegradable medical implement can be dissolved in vivo at an appropriate dissolution rate.

DESCRIPTION OF THE EMBODIMENT

Hereinafter, a biodegradable medical implement according to an embodiment of the present invention will be described with reference to the drawings.

Examples of the biodegradable medical implement according to the embodiment of the present invention include a plate, a pin, a screw, and the like used, for example, to attach or fix a bone in the body.

The biodegradable medical implement is formed of a pure magnesium material containing 99.9% by mass or more of magnesium, the pure magnesium material includes an unavoidable impurity in addition to magnesium. Examples of the unavoidable impurity include Zn, Zr, and Mn. However, any type of pure magnesium materials may be used.

The corrosion resistance (dissolubility) of the biodegradable medical implement changes depending on the orientation of the magnesium crystal grains with respect to the surface of the biodegradable medical implement. That is, the magnesium crystal grains have a hexagonal close-packed structure, and when a (0001) plane in the hexagonal close-packed structure is oriented toward a surface side of the biodegradable medical implement, the corrosion resistance of the biodegradable medical implement improves (the dissolubility is decreased).

Thus, the orientation of the magnesium crystal grains with respect to the surface of the biodegradable medical implement is detected by using the electron back-scatter diffraction (EBSD) method, and a corrosion resistance evaluation test is performed for the biodegradable medical implement.

Note that the equipment used in the evaluation test by EBSD is as follows.

Figure 1A:
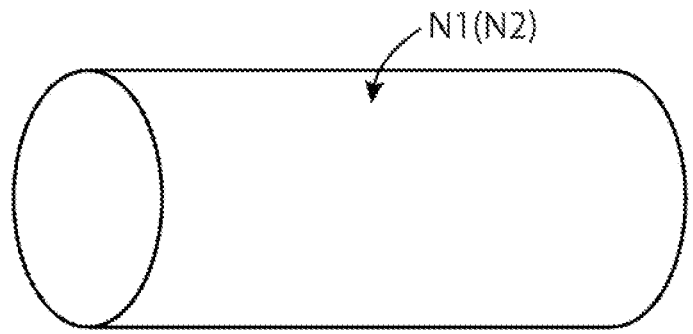
FIG. 1A to FIG. 1C are diagrams illustrating a sample used for an evaluation test in an embodiment of the present invention.

(SEM observation, EDS analysis)
Scanning electron microscope (SEM) JEOL Ltd. JSM-IT300HR(LA)
Energy-dispersive X-ray spectroscopy (EDS) JEOL Ltd. JED-2300 Analysis Station Plus
(EBSD data acquisition software (software for controlling SEM stage, calculating crystal orientation, etc.))
TSL Solutions Co., Ltd. OIM Data Collection
(EBSD data analysis software (software for analyzing acquired data in detail and creating maps, graphs, etc.))
TSL Solutions Co., Ltd. OIM Analysis In the present embodiment, as s sample corresponding to the biodegradable medical implement, two types of cylindrical samples N1 and N2 each having a circular cross section with a diameter of 2 mm and a length of 5 mm, as shown in FIG. 1A, are used.

Note that, in the present embodiment, (Sample N1) and (Sample N2) in use are obtained by cutting or drawing an extruded material obtained by extrusion molding. In the case of cutting, the extruded material is cut while being rotated at a predetermined rotating speed to obtain a desired shape. Further, in the case of drawing, a desired shape is obtained by drawing the extruded material using a drawing die while a heat treatment (annealing) is appropriately applied to the extruded material. A longitudinal direction of (Sample N1) and (Sample N2) coincides with the extrusion direction in the extrusion molding. In this manner, for example, in cutting, drawing, or the like, a predetermined stress is applied to the entire circumference of the sample while the grain size of the crystal grains of the sample is adjusted by the heat treatment or processing heat. This makes it possible to form well-oriented layers inside the sample over the entire circumference. Note that the processing method for applying a predetermined stress to the entire circumference of the sample is not limited to cutting and drawing.

(Orientation of Magnesium Crystal Grains)

Figure 1B:
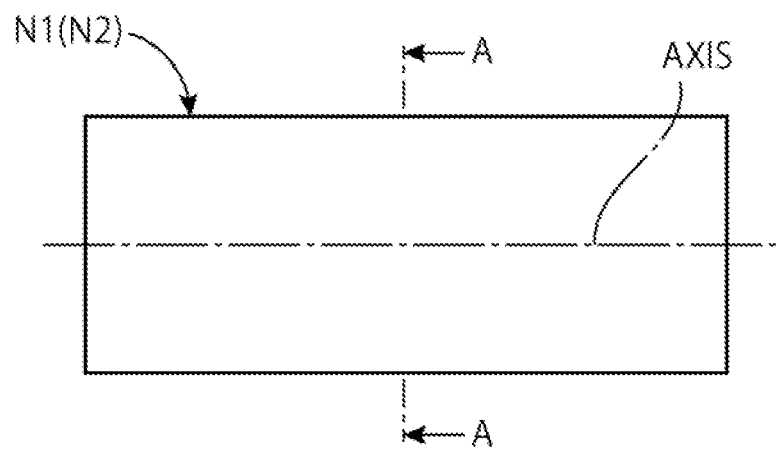
Figure 1C:
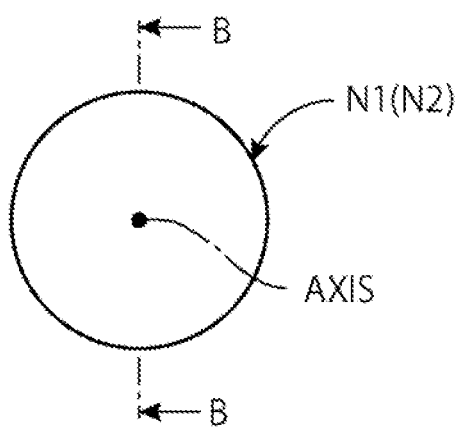

First, for (Sample N1) and (Sample N2), the orientation of the magnesium crystal grains with respect to the surface of the sample is detected by the electron back-scatter diffraction in a transverse section cut along a plane perpendicular to the axis (A-A line cross section in FIG. 1B) as shown in FIG. 1B and in a longitudinal section cut in parallel to the axis through the axis (B-B line cross section in FIG. 1C) as shown in FIG. 1C.

(Orientation in Transverse Section)

Figure 2:
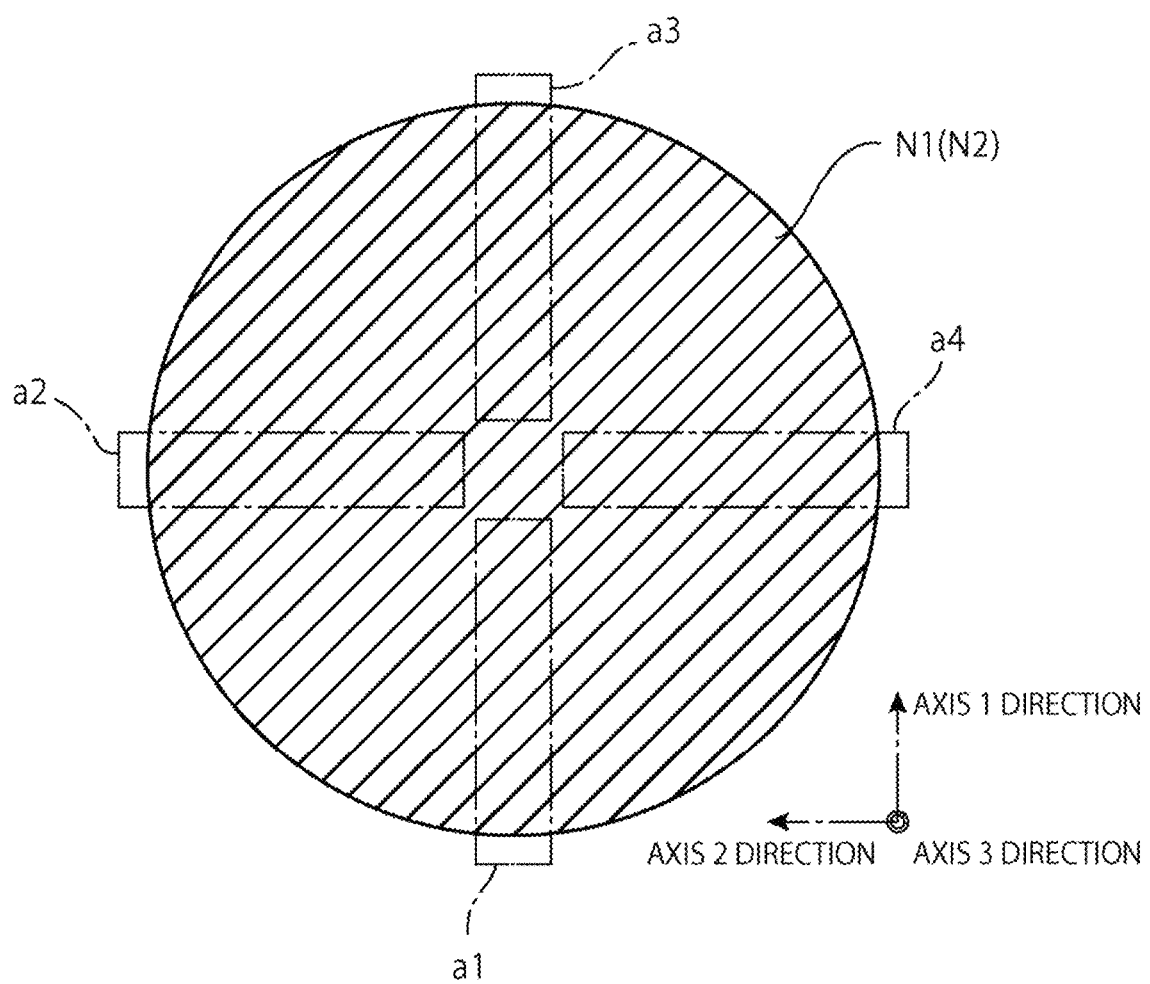
FIG. 2 is a diagram (enlarged cross-sectional view taken along a line A-A in FIG. 1B) illustrating observation points in a transverse section of the sample.

In the transverse section, the orientation of the magnesium crystal grains is detected when an observation point a1 shown in FIG. 2 is observed from three directions. In FIG. 2, as three directions, an axis 1 direction, an axis 2 direction, and an axis 3 direction for observing the observation point a1 are shown. The observation from the three directions includes observation from the outside in a direction parallel to the transverse section and perpendicular with respect to the surface of the sample (observation from the axis 1 direction), observation from a direction parallel to the transverse section and perpendicular to the axis 1 direction (observation from the axis 2 direction), and observation from a direction perpendicular to the transverse section (observation from the axis 3 direction). Note that the axis 3 direction is a direction perpendicular to the plane of the paper of FIG. 2.

Figure 3:
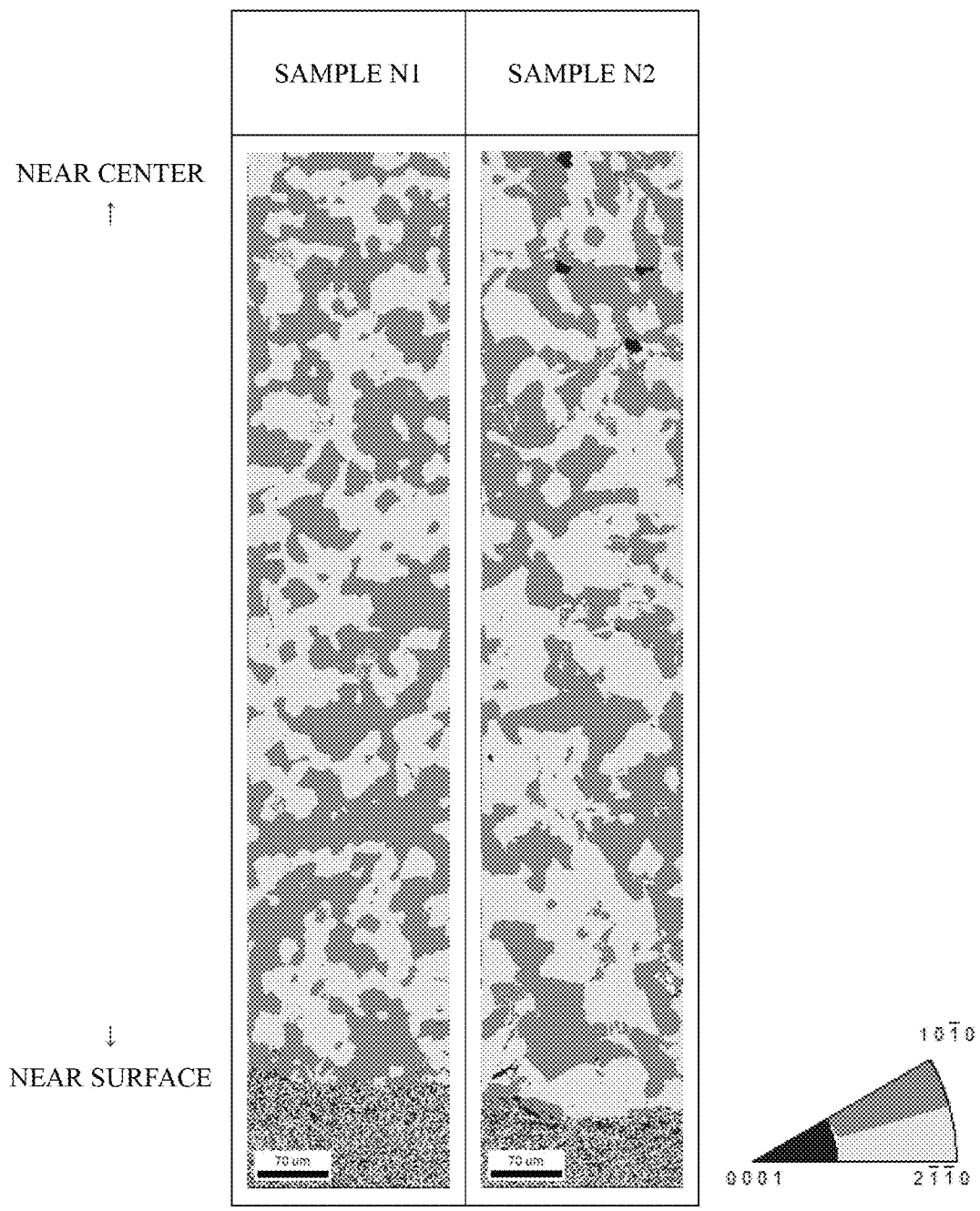
FIG. 3 is a diagram illustrating orientation of magnesium crystal grains when the transverse section is observed from an axis 3 direction.

FIG. 3 shows the orientation of the magnesium crystal grains when the observation point a1 in the transverse section is observed from the axis 3 direction. Thus, the orientation of the magnesium crystal grains observed from the axis 3 directions shown in FIG. 3 shows the orientation of the magnesium crystal grains that actually appears in the transverse section. That is, it shows which plane of the magnesium crystal grains faces the axis 3 direction when the transverse section is observed from the axis 3 direction.

In FIG. 3, regarding the orientation of the magnesium crystal grains, as shown in the lower right of the figure, the magnesium crystal grains in which the (0001) plane in the hexagonal crystal structure is inclined by 0 to 45 degrees with respect to the axis 3 direction, which is the observation direction, are shown in black color, the magnesium grains in which a (10-10) plane is inclined by 0 to 45 degrees with respect to the axis 3 direction, which is the observation direction, are shown in dark gray color, and the magnesium crystal grains in which a (2-1-10) plane is inclined by 0 to 45 degrees with respect to the axis 3 direction, which is the observation direction, are shown in light gray color.

Note that, regarding the orientation of the magnesium crystal grains shown in FIG. 3, the sentence "the (0001) plane in the hexagonal crystal structure is inclined by 0 to 45 degrees with respect to the axis 3 direction, which is the observation direction" means that "the normal direction of the (0001) plane in the hexagonal crystal structure is inclined by 0 to 45 degrees with respect to the normal direction of the surface". In that case, the direction of inclination may be any direction. In the following diagrams showing the orientation of the magnesium crystal grains, the observation direction may be different from that in FIG. 3, but the method of showing the orientation of the magnesium crystal grains is the same as in FIG. 3.

According to FIG. 3, when (Sample N1) and (Sample N2) are observed from the axis 3 direction, it is found that, in both samples, most of the crystal grains are the crystal grains shown in dark gray color and the crystal grains shown in light gray color, and there are almost no crystal grains shown in black color, over the entire area from near the surface of the sample to near the center.

Figure 4:
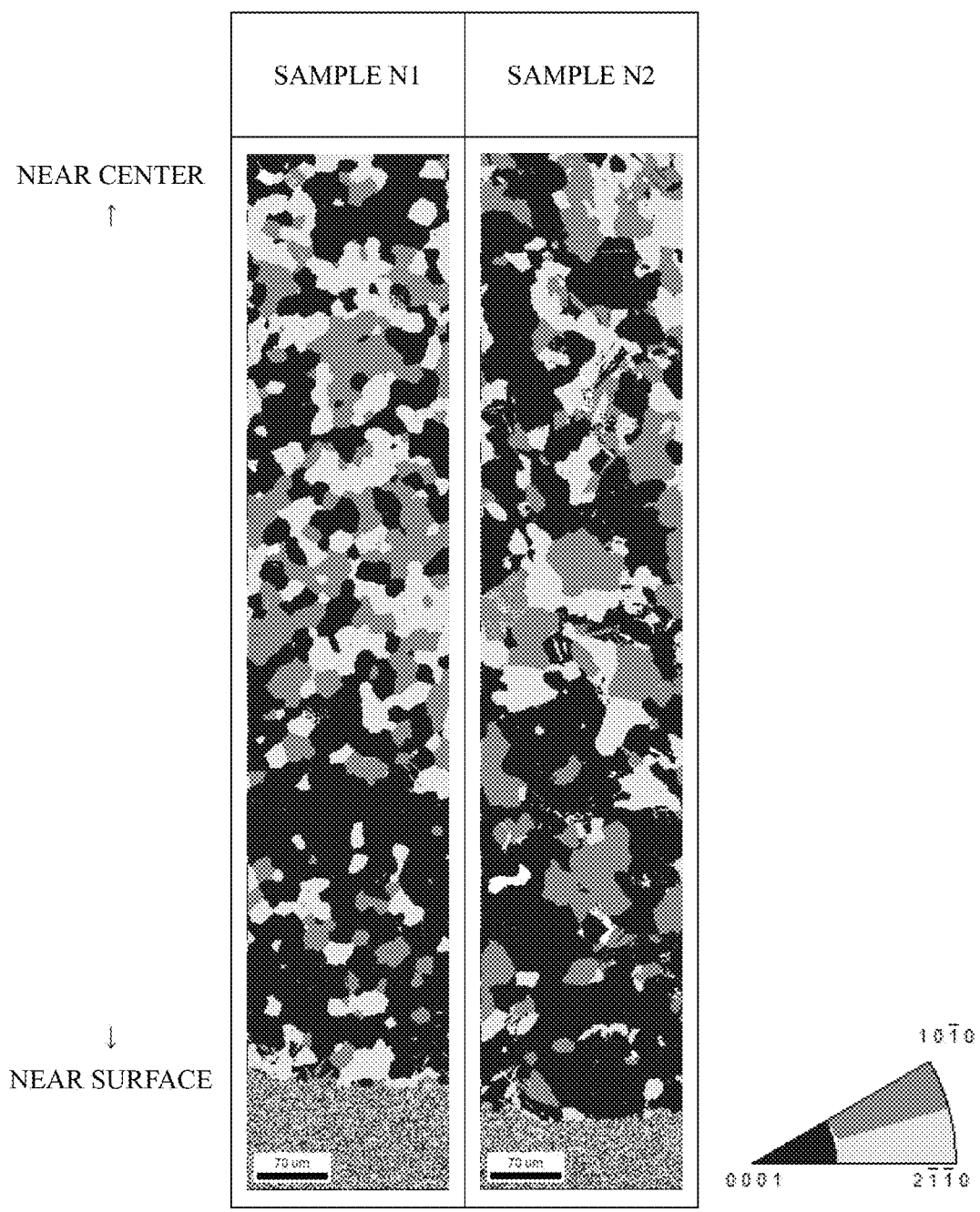
FIG. 4 is a diagram illustrating the orientation of the magnesium crystal grains when the transverse section is observed from an axis 1 direction.

FIG. 4 shows the orientation of the magnesium crystal grains when the observation point a1 in the transverse section is observed from the axis 1 direction, the orientation being obtained by calculation based on the result of observation from the axis 3 direction shown in FIG. 3.

According to FIG. 4, when (Sample N1) and (Sample N2) are observed from the axis 1 direction, it is found that, in both samples, the crystal grains shown in black color, the crystal grains shown in dark gray color, and the crystal grains shown in light gray color are mixed over the entire area from near the surface of the sample to near the center. In particular, in both (Sample N1) and (Sample N2), it is found that there are more crystal grains shown in black color near the surface of the sample than near the center of the sample.

Figure 5:
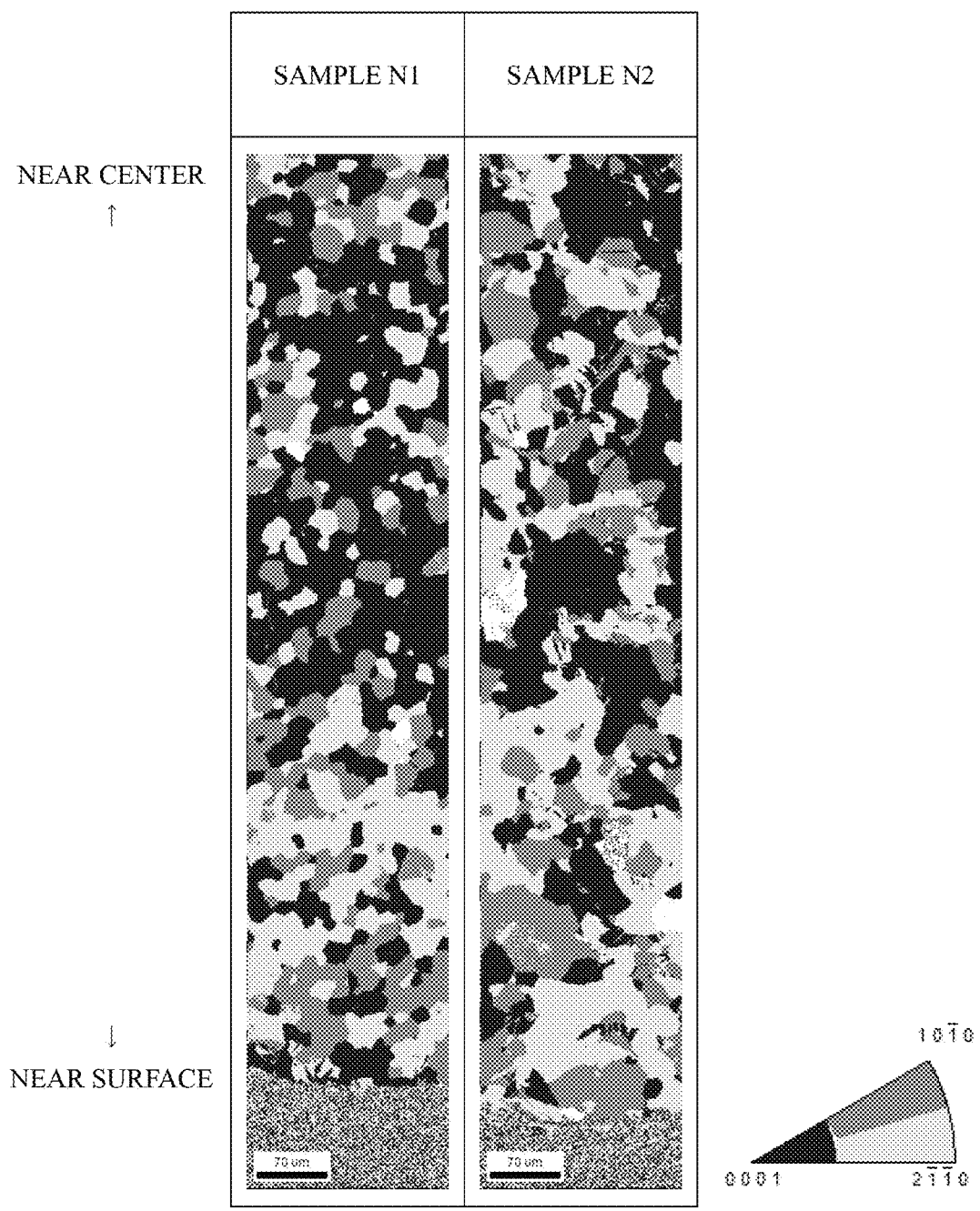
FIG. 5 is a diagram illustrating the orientation of the magnesium crystal grains when the transverse section is observed from an axis 2 direction.

FIG. 5 shows the orientation of the magnesium crystal grains when the observation point a1 in the transverse section is observed from the axis 2 direction, the orientation being obtained by calculation based on the result of observation from the axis 3 direction shown in FIG. 3.

According to FIG. 5, when (Sample N1) and (Sample N2) are observed from the axis 2 direction, it is found that, in both samples, the crystal grains shown in black color, the crystal grains shown in dark gray color, and the crystal grains shown in light gray color are mixed over the entire area from near the surface of the sample to near the center. In particular, in both (Sample N1) and (Sample N2), it is found that there are many crystal grains shown in black color near the center of the sample, and there are few crystal grains shown in black color near the surface of the sample.

As described above, when the observation point a1 in the transverse section of the sample is observed from the axis 1 direction, that is, a direction from the outer peripheral surface of the sample toward the center, as shown in FIG. 4, many crystal grains shown in black color are observed.

In the present embodiment, the crystal grains shown in black color in FIG. 4 are "the magnesium crystal grains in which the (0001) plane in the hexagonal crystal structure is arranged perpendicular with respect to the normal direction of the surface" or "the magnesium crystal grains in which the normal direction of the (0001) plane in the hexagonal crystal structure is inclined by 0 to 45 degrees with respect to the normal direction of the surface (the direction of inclination may be in any direction)". These magnesium crystal grains are referred to as "magnesium crystal grains in which the (0001) plane in the hexagonal crystal structure is oriented toward the surface side of the sample".

Note that when the observation point a1 is observed from the axis 1 direction, as shown in FIG. 4, many magnesium crystal grains in which the (0001) plane in the hexagonal crystal structure is oriented toward the surface side of the sample are observed. Based on FIG. 3 to FIG. 5, it is found that the (0001) planes of these magnesium crystal grains have a strong tendency to be inclined in a direction perpendicular to the longitudinal direction.

That is, it is found that many of the crystal grains shown in black color in FIG. 4 are the magnesium crystal grains in which the (0001) plane in the hexagonal crystal structure is arranged perpendicular with respect to the normal direction of the outer peripheral surface or the magnesium crystal grains in which the (0001) plane in the hexagonal crystal structure is included in any of planes obtained by inclining the plane perpendicular with respect to the normal direction of the outer peripheral surface by 0 to 45 degrees around a straight line along the longitudinal direction (a direction perpendicular to the transverse section).

(Orientation in Longitudinal Section)

Figure 6:
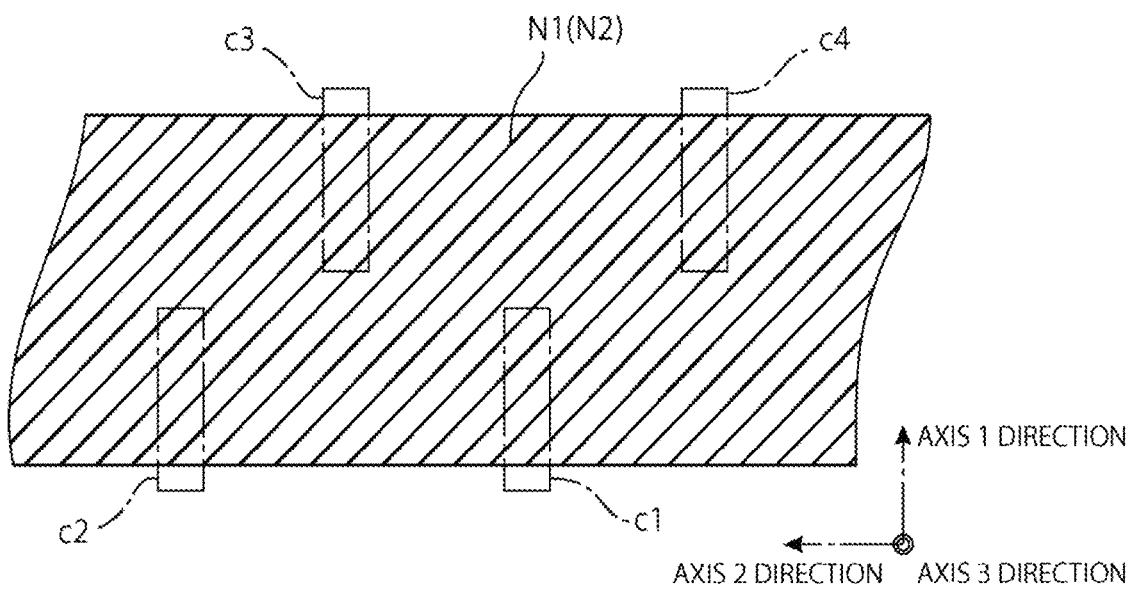
FIG. 6 is a diagram (enlarged cross-sectional view of an essential part taken along a line B-B in FIG. 1C) illustrating observation points in a longitudinal section of the sample.

In the longitudinal section, the orientation of the magnesium crystal grains is detected when the observation point c1 shown in FIG. 6 is observed from three directions. In FIG. 6, as three directions, an axis 1 direction, an axis 2 direction, and an axis 3 direction for observing the observation point c1 are shown. The observation from the three directions includes observation from the outside in a direction parallel to the longitudinal section and perpendicular with respect to the surface of the sample (observation from the axis 1 direction), observation from a direction parallel to the longitudinal section and perpendicular to the axis 1 direction (observation from the axis 2 direction), and observation from a direction perpendicular to the longitudinal section (observation from the axis 3 direction). Note that the axis 3 direction is a direction perpendicular to the plane of the paper of FIG. 6.

Figure 7:
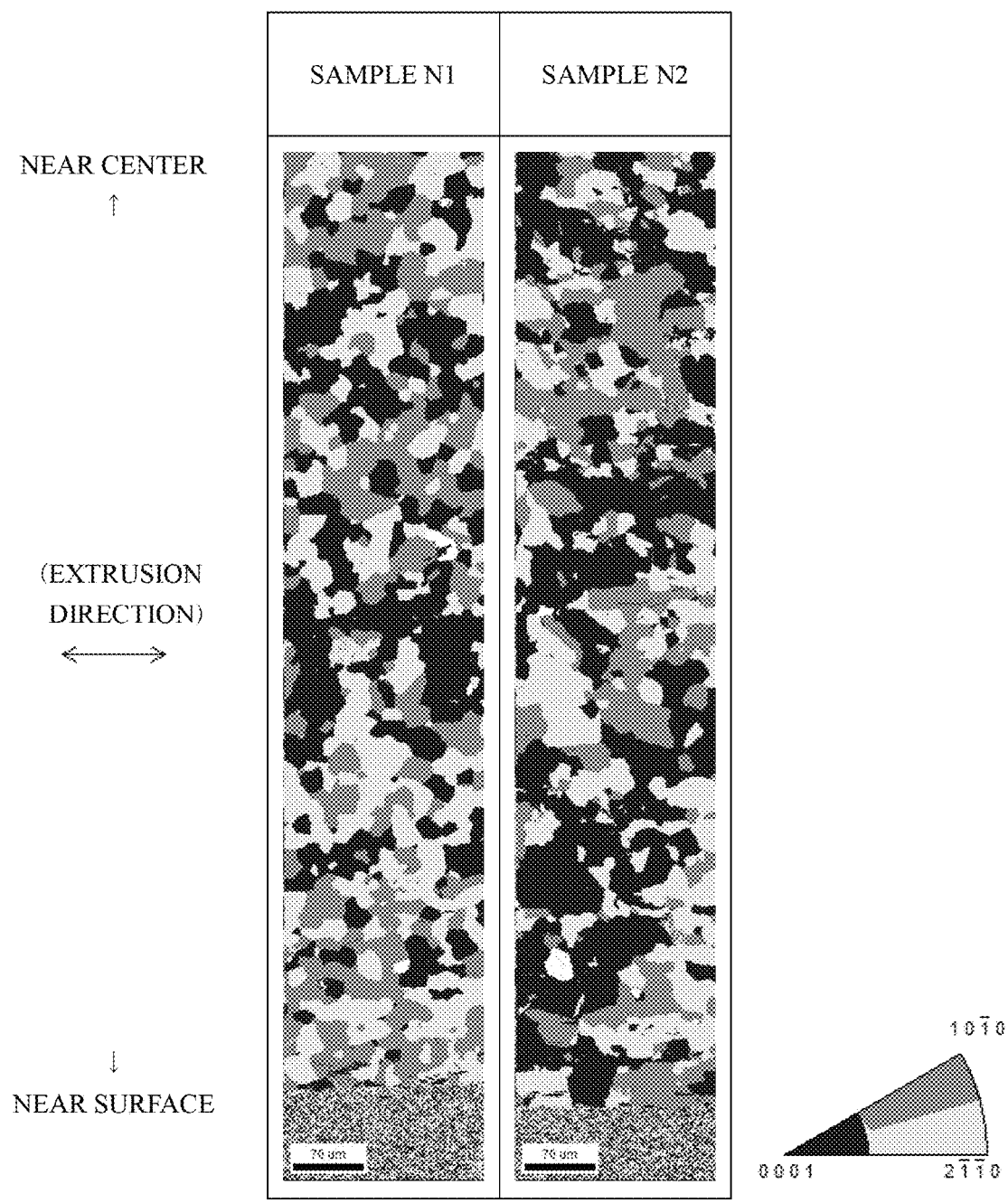
FIG. 7 is a diagram illustrating the orientation of the magnesium crystal grains when the longitudinal section is observed from the axis 3 direction.

FIG. 7 shows the orientation of the magnesium crystal grains when the observation point c1 in the longitudinal section is observed from the axis 3 direction. Thus, the orientation of the magnesium crystal grains observed from the axis 3 direction shown in FIG. 7 shows the orientation of the magnesium crystal grains that actually appears in the longitudinal section. That is, it shows which plane of the magnesium crystal grains faces the axis 3 direction when the longitudinal section is observed from the axis 3 direction.

According to FIG. 7, when (Sample N1) and (Sample N2) are observed from the axis 3 direction, it is found that, in both samples, the crystal grains shown in black color, the crystal grains shown in dark gray color, and the crystal grains shown in light gray color are mixed over the entire area from near the surface of the sample to near the center.

Figure 8:
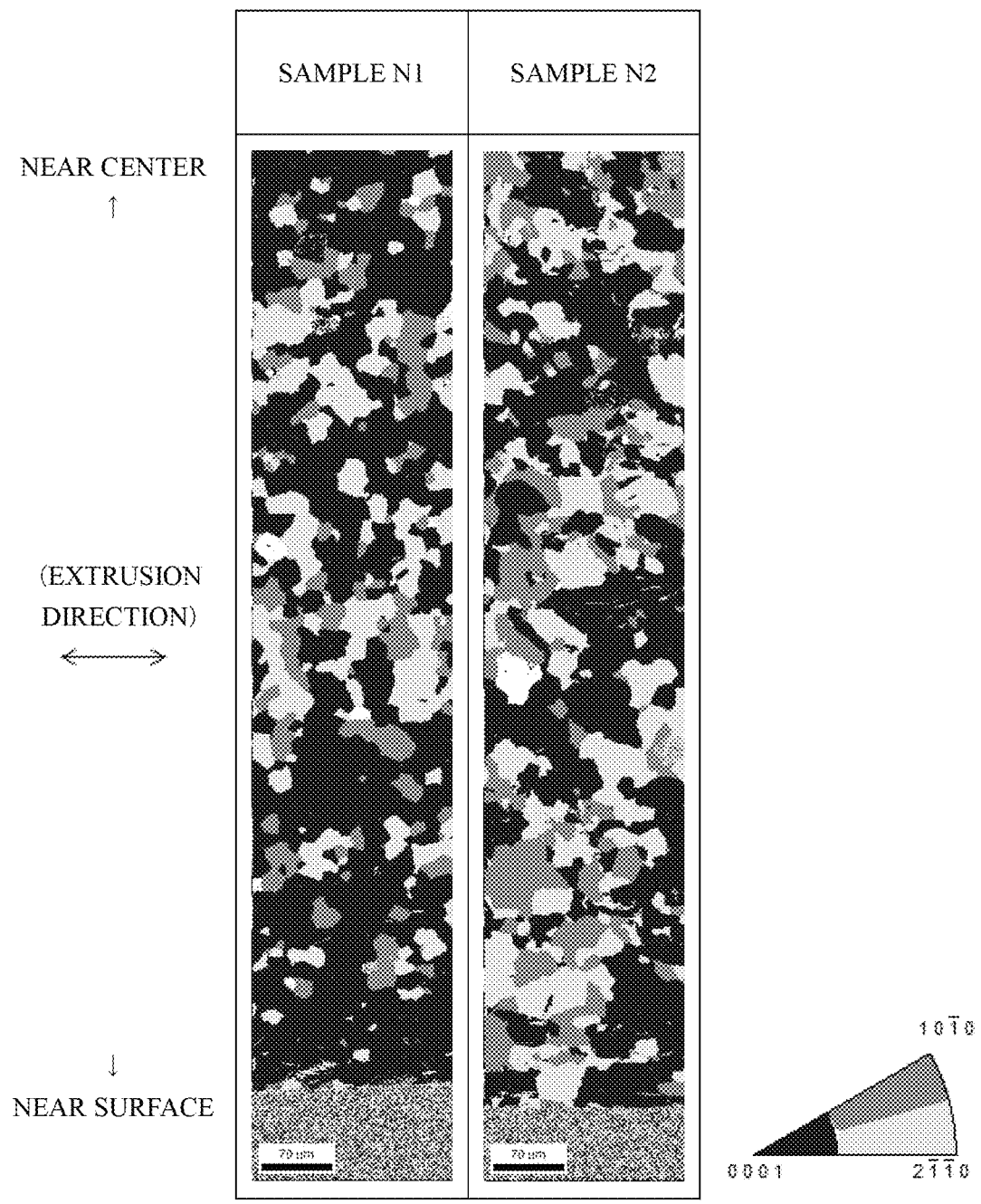
FIG. 8 is a diagram illustrating the orientation of the magnesium crystal grains when the longitudinal section is observed from the axis 1 direction.

FIG. 8 shows the orientation of the magnesium crystal grains when the observation point c1 in the longitudinal section is observed from the axis 1 direction, the orientation being obtained by calculation based on the result of observation from the axis 3 direction shown in FIG. 7.

According to FIG. 8, when (Sample N1) and (Sample N2) are observed from the axis 1 direction, it is found that, in both samples, the crystal grains shown in black color, the crystal grains shown in dark gray color, and the crystal grains shown in light gray color are mixed over the entire area from near the surface of the sample to near the center. In particular, it is found that there are more crystal grains shown in black color near the surface of (Sample N1) than near the center of the sample.

Figure 9:
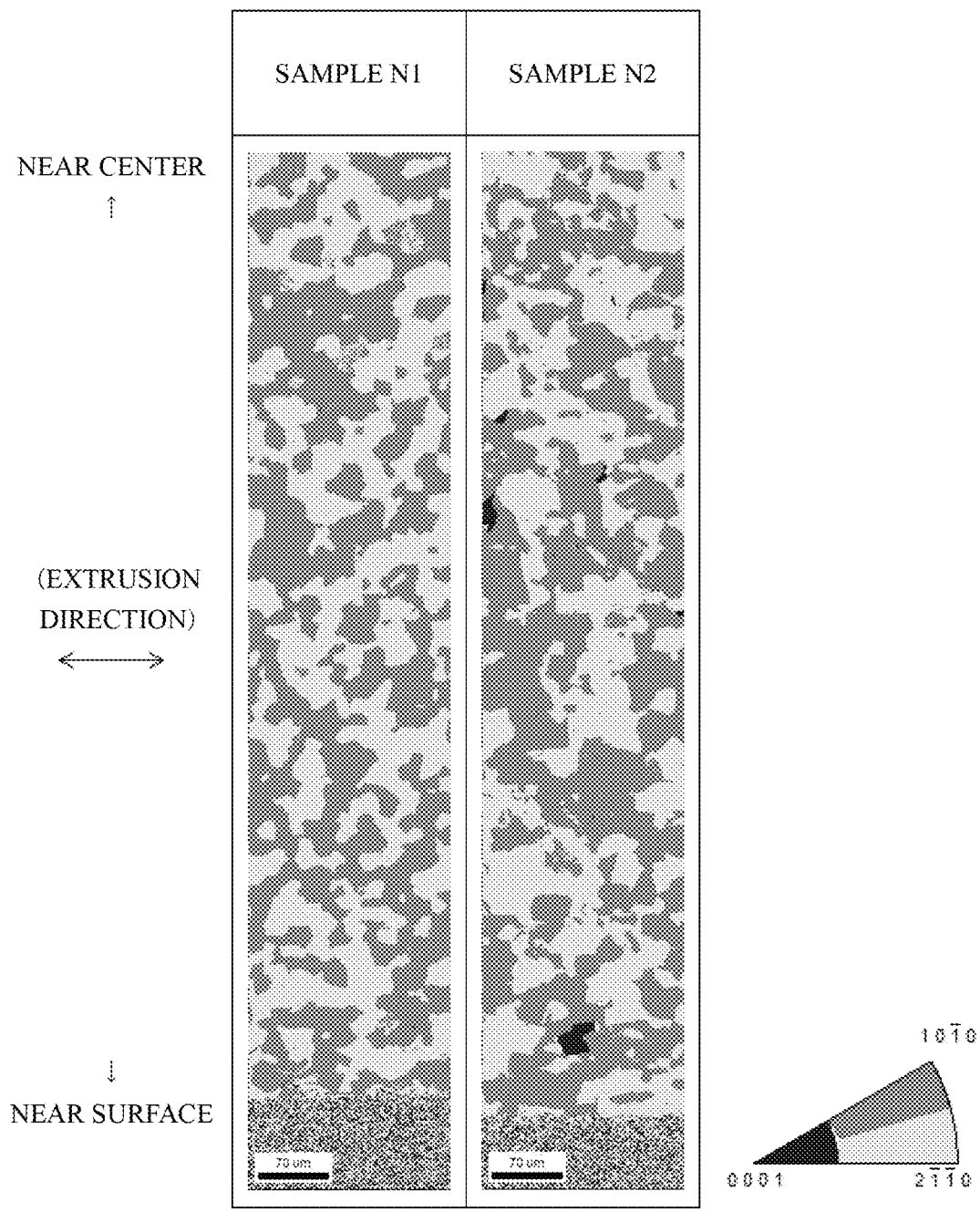
FIG. 9 is a diagram illustrating the orientation of the magnesium crystal grains when the longitudinal section is observed from the axis 2 direction.

FIG. 9 shows the orientation of the magnesium crystal grains when the observation point c1 in the longitudinal section is observed from the axis 2 direction, the orientation being obtained by calculation based on the result of observation from the axis 3 direction shown in FIG. 7.

According to FIG. 9, when (Sample N1) and (Sample N2) are observed from the axis 2 direction, it is found that, in both samples, most of the crystal grains are the crystal grains shown in dark gray color and the crystal grains shown in light gray color, and there are almost no crystal grains shown in black color over the entire area from near the surface of the sample to near the center.

As described above, when the observation point c1 in the longitudinal section of the sample is observed from the axis 1 direction, that is, a direction from the outer peripheral surface of the sample toward the center, as shown in FIG. 8, many crystal grains shown in black color are observed.

In the present embodiment, the crystal grains shown in black color in FIG. 8 are "the magnesium crystal grains in which the (0001) plane in the hexagonal crystal structure is arranged perpendicular with respect to the normal direction of the surface" or "the magnesium crystal grains in which the normal direction of the (0001) plane in the hexagonal crystal structure is inclined by 0 to 45 degrees with respect to the normal direction of the surface (the direction of inclination may be in any direction)".

Note that when the observation point c1 is observed from the axis 1 direction, as shown in FIG. 8, many magnesium crystal grains in which the (0001) plane in the hexagonal crystal structure is oriented toward the surface side of the sample are observed. Based on FIG. 7 to FIG. 9, it is found that the (0001) planes of these magnesium crystal grains have a strong tendency to be inclined in the direction perpendicular to the longitudinal direction of the sample. This point is the same for the orientation in the longitudinal section as the orientation in the transverse section.

(Orientation in Entire Circumference of Sample)

In the present embodiment, both (Sample N1) and (Sample N2) are obtained by cutting or drawing the extruded material obtained by extrusion molding. Thus, in the transverse section of the sample, the orientation of the magnesium crystal grains with respect to the surface of the sample is considered approximately the same over the entire circumference of the sample.

In order to confirm that the orientation of the magnesium crystal grains in the transverse section of the sample is substantially the same over the entire circumference, the orientation of the magnesium crystal grains is detected at observation points a2 to a4 in addition to the observation point a1 described above in the transverse section shown in FIG. 2. The observation points a1 to a4 in the transverse section are points separated from each other by 90 degrees in the circumferential direction on the surface of the sample.

Figure 10:
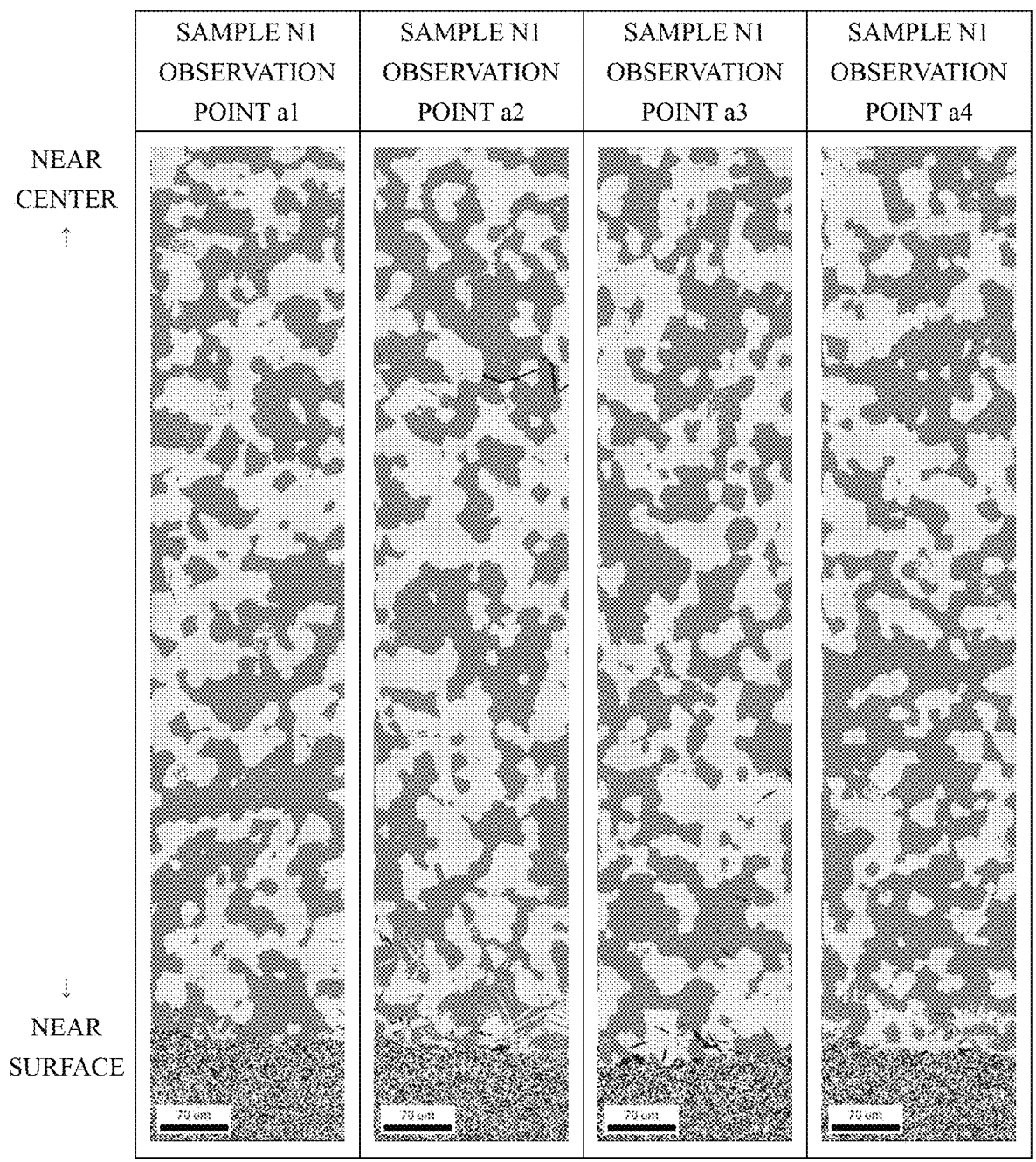
FIG. 10 is a diagram illustrating the orientation of the magnesium crystal grains when observation points a1 to a4 in the transverse section of (Sample N1) are observed from the axis 3 direction.
Figure 11:
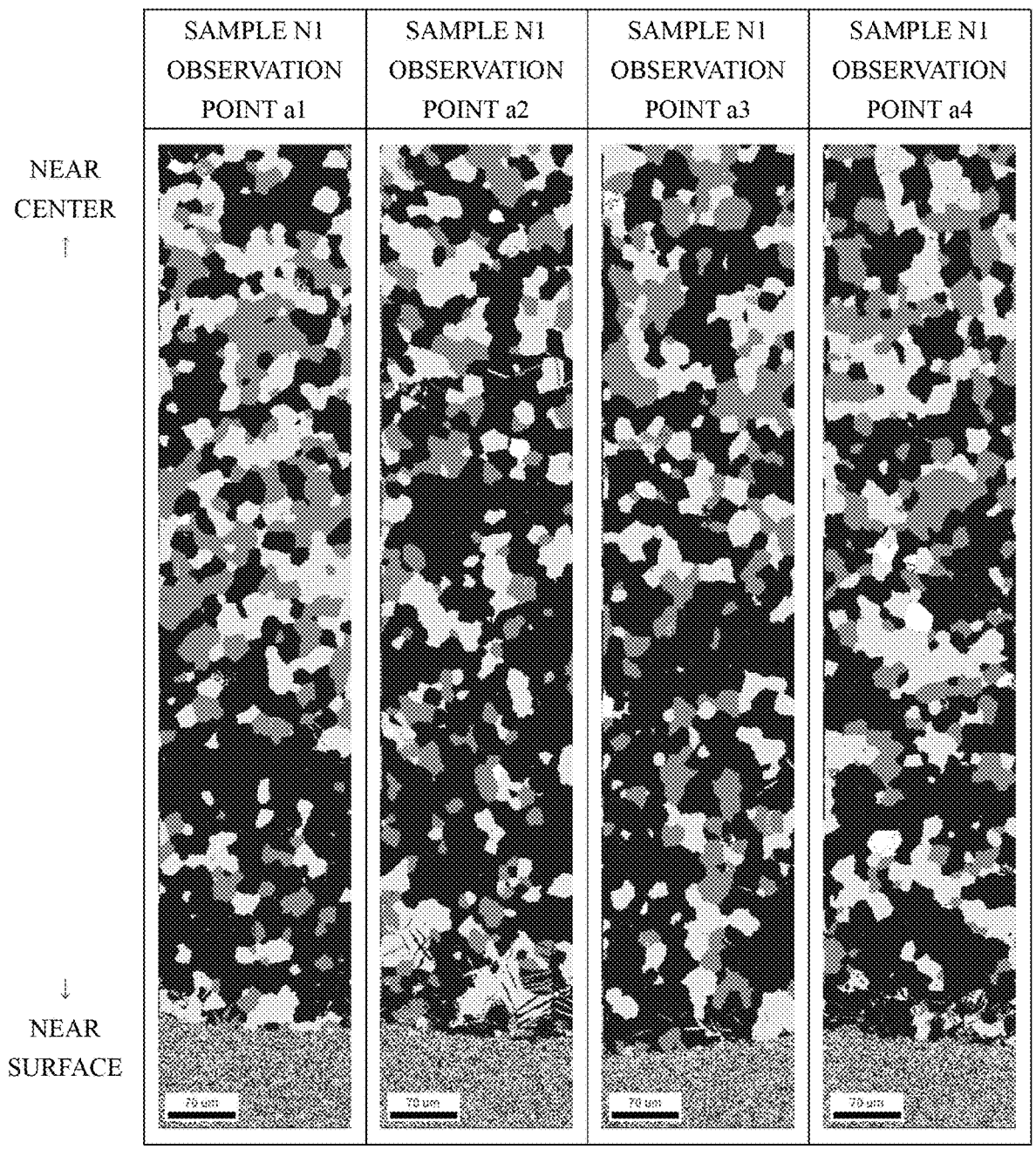
FIG. 11 is a diagram illustrating the orientation of the magnesium crystal grains when the observation points a1 to a4 in the transverse section of (Sample N1) are observed from the axis 1 direction.
Figure 12:
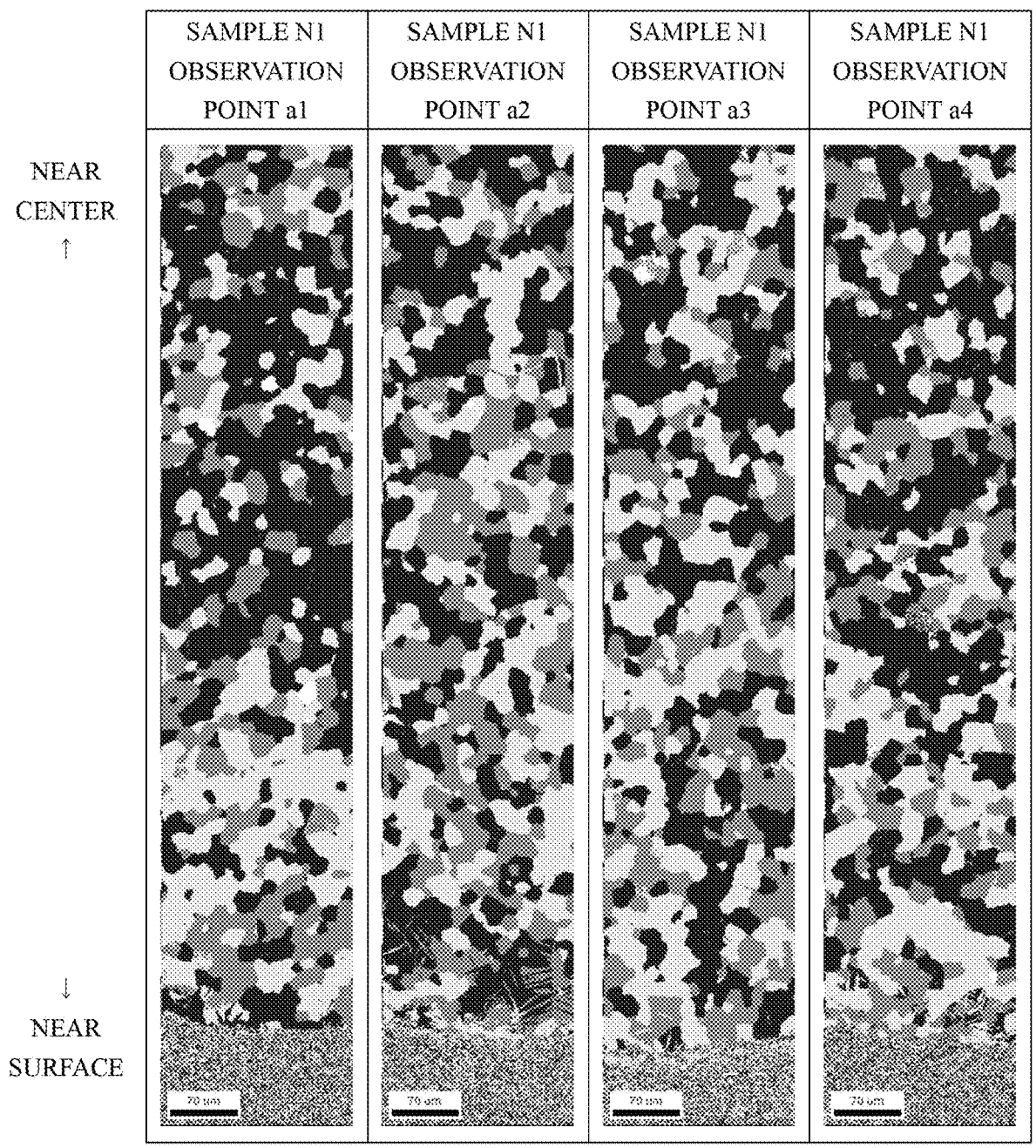
FIG. 12 is a diagram illustrating the orientation of the magnesium crystal grains when the observation points a1 to a4 in the transverse section of (Sample N1) are observed from the axis 2 direction.

FIG. 10 to FIG. 12 show the orientation of the magnesium crystal grains when the observation points a1 to a4 in the transverse section of (Sample N1) are observed from the axis 3 direction, the axis 1 direction, and the axis 2 direction, respectively. According to FIG. 10 to FIG. 12, it is found that the orientation of the magnesium crystal grains is substantially the same at the points separated from each other by 90 degrees in the circumferential direction in the transverse section of (Sample N1).

Figure 13:
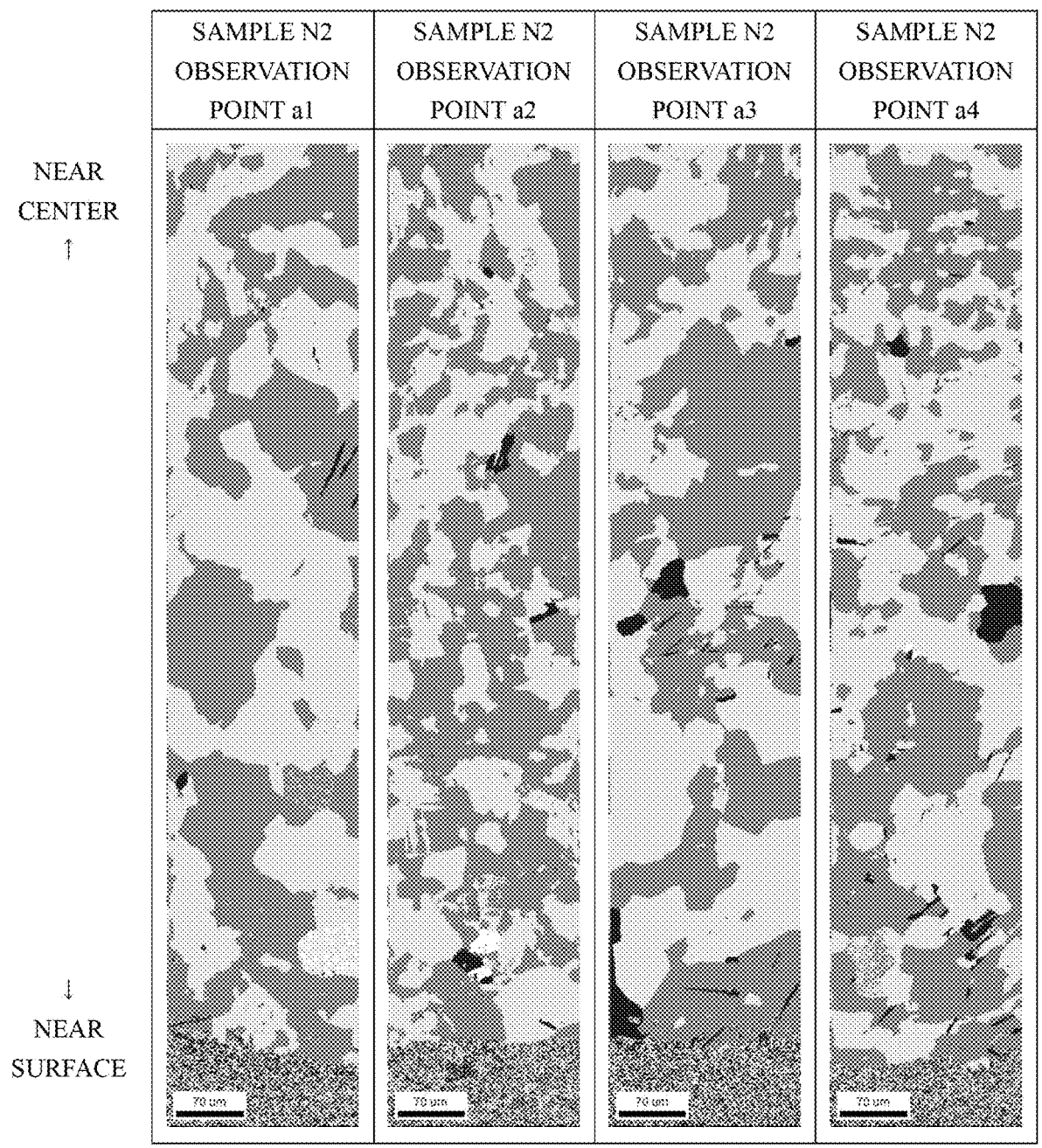
FIG. 13 is a diagram illustrating the orientation of the magnesium crystal grains when observation points a1 to a4 in the transverse section of (Sample N2) are observed from the axis 3 direction.
Figure 14:
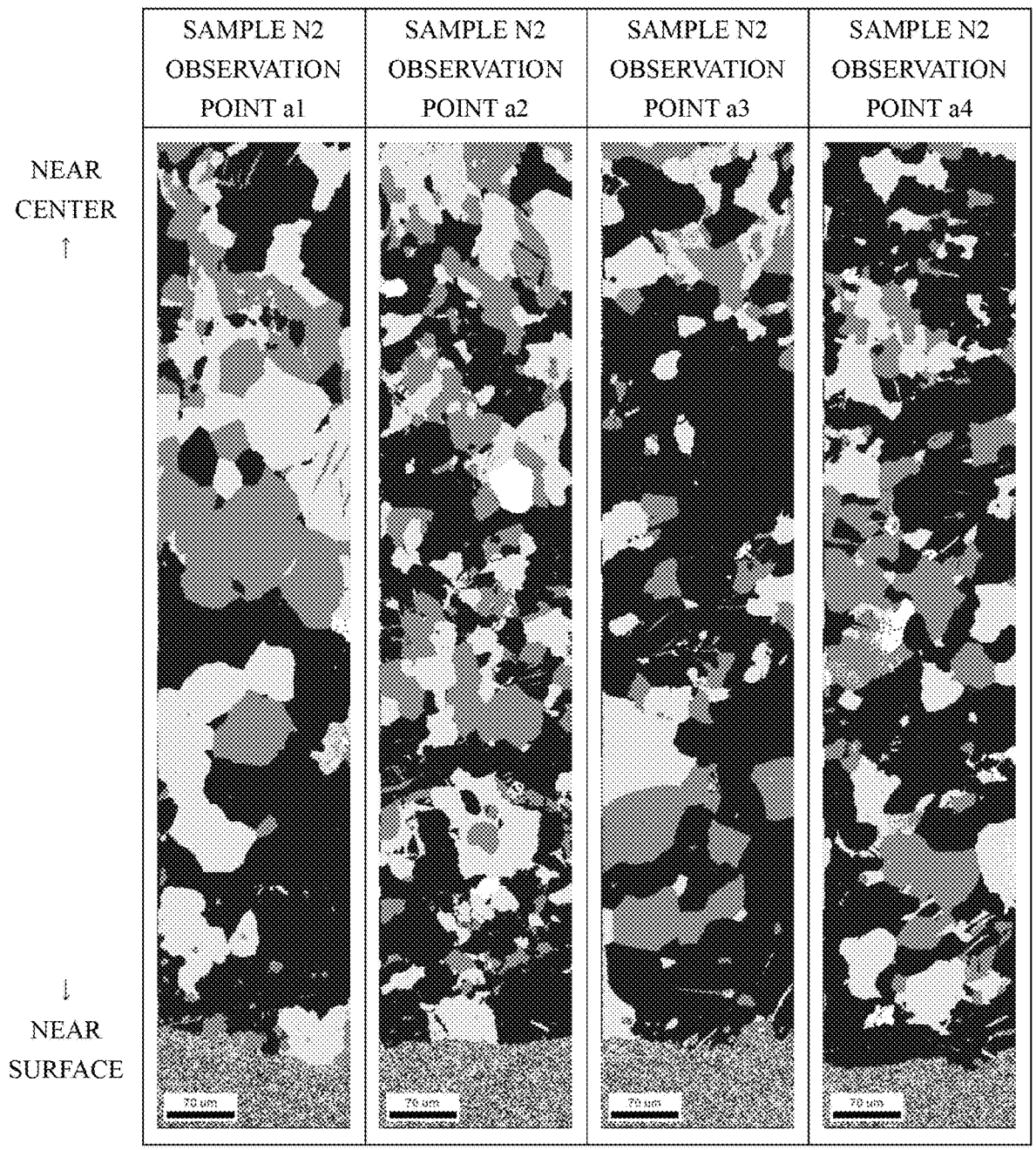
FIG. 14 is a diagram illustrating the orientation of the magnesium crystal grains when the observation points a1 to a4 in the transverse section of (Sample N2) are observed from the axis 1 direction.
Figure 15:
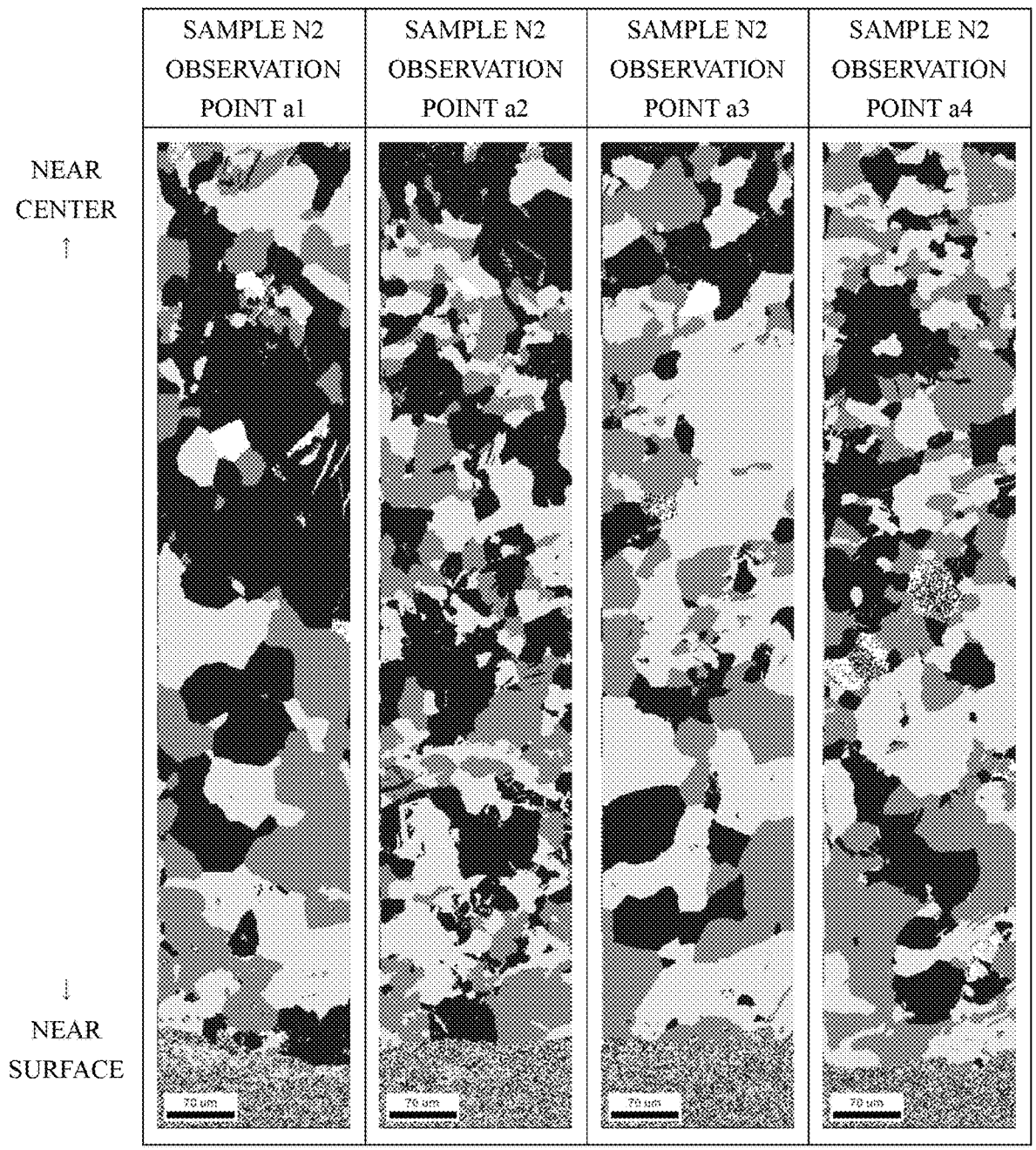
FIG. 15 is a diagram illustrating the orientation of the magnesium crystal grains when the observation points a1 to a4 in the transverse section of (Sample N2) are observed from the axis 2 direction.
Figure 15:
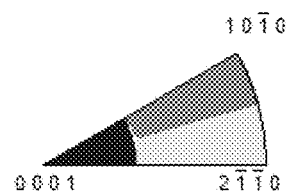

FIG. 13 to FIG. 15 show the orientation of the magnesium crystal grains when the observation points a1 to a4 in the transverse section of (Sample N2) are observed from the axis 3 direction, the axis 1 direction, and the axis 2 direction, respectively. According to FIG. 13 to FIG. 15, it is found that, like (Sample N1), the orientation of the magnesium crystal grains is substantially the same at the points separated from each other by 90 degrees in the circumferential direction in the transverse section of (Sample N2).

Specifically, according to FIG. 10 and FIG. 13, it is found that there are almost no crystal grains shown in black color. According to FIG. 11 and FIG. 14, it is found that there are more crystal grains shown in black color near the surface of the sample than near the center of the sample. According to FIG. 12 and FIG. 15, it is found that there are fewer crystal grains shown in black color near the surface of the sample than near the center of the sample.

(Orientation in Longitudinal Direction of Sample)

Further, (Sample N1) and (Sample N2) are both obtained by cutting or drawing the extruded material obtained by extrusion molding. Thus, in the longitudinal section of the sample, the orientation of the magnesium crystal grains with respect to the surface of the sample is considered approximately the same along most of its longitudinal direction.

In order to confirm that the orientation of the magnesium crystal grains is substantially the same along most of its longitudinal direction, the orientation of the magnesium crystal grains is detected at observation points c2 to c4 in addition to the observation point c1 described above in the longitudinal section shown in FIG. 6. The observation points c1 and c2 are two points separated in the longitudinal direction on one surface along the longitudinal direction in the longitudinal section of the sample, and the observation points c3 and c4 are two points separated in the longitudinal direction on the other surface along the longitudinal direction in the longitudinal section of the sample.

Figure 16:
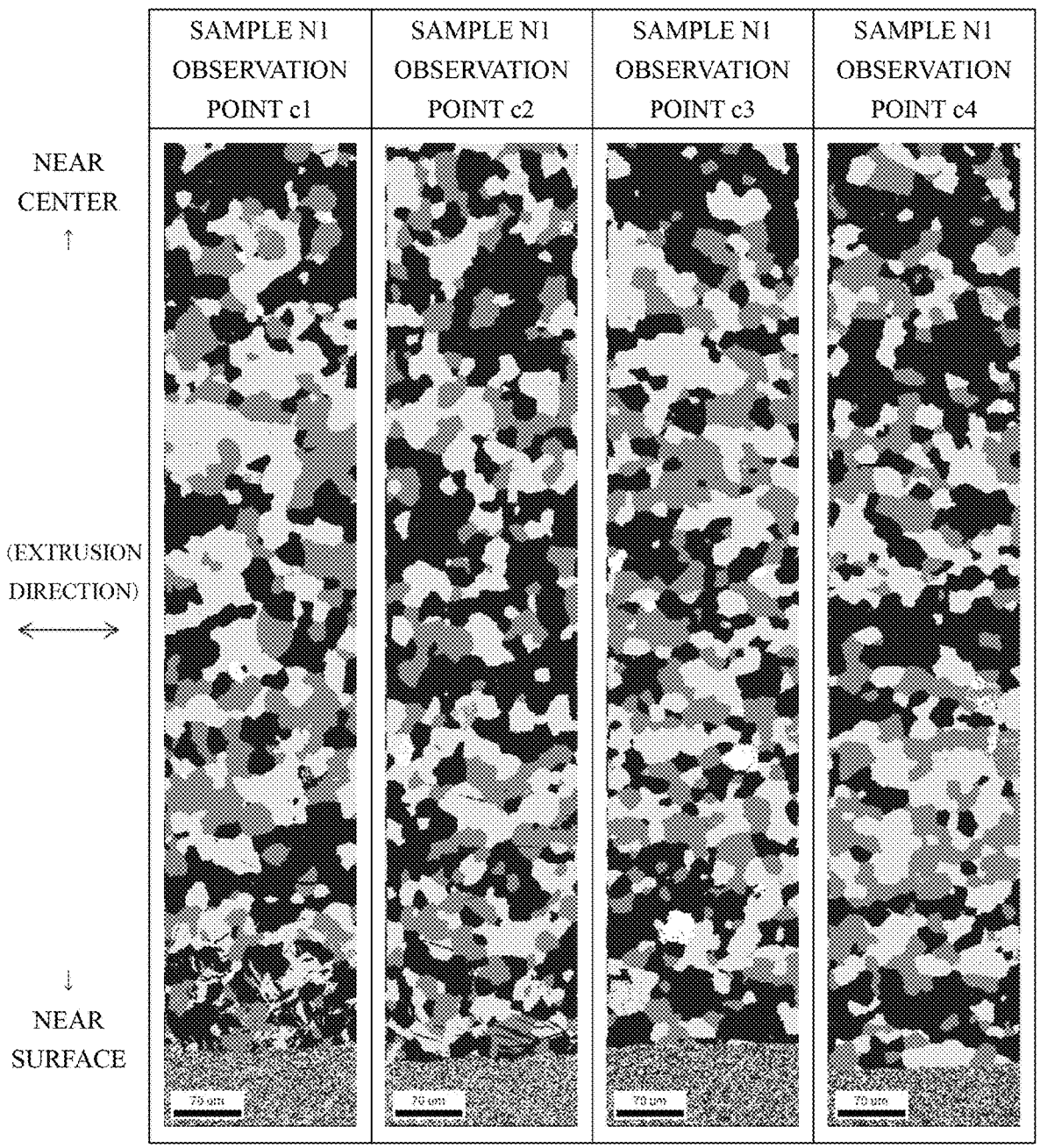
FIG. 16 is a diagram illustrating the orientation of the magnesium crystal grains when observation points c1 to c4 in the longitudinal section of (Sample N1) are observed from the axis 3 direction.
Figure 17:
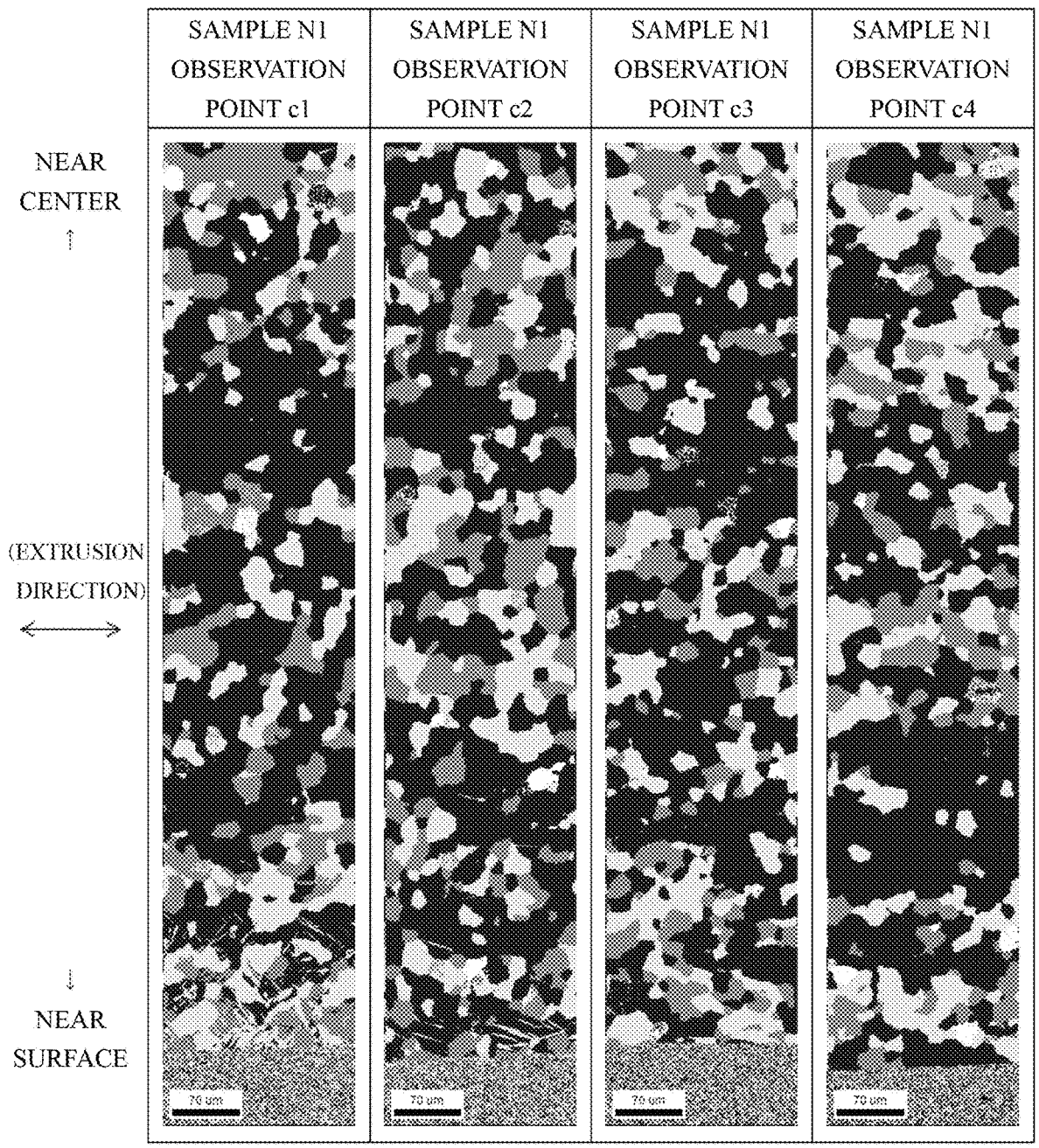
FIG. 17 is a diagram illustrating the orientation of the magnesium crystal grains when the observation points c1 to c4 in the longitudinal section of (Sample N1) are observed from the axis 1 direction.
Figure 17:
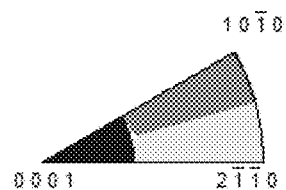
Figure 18:
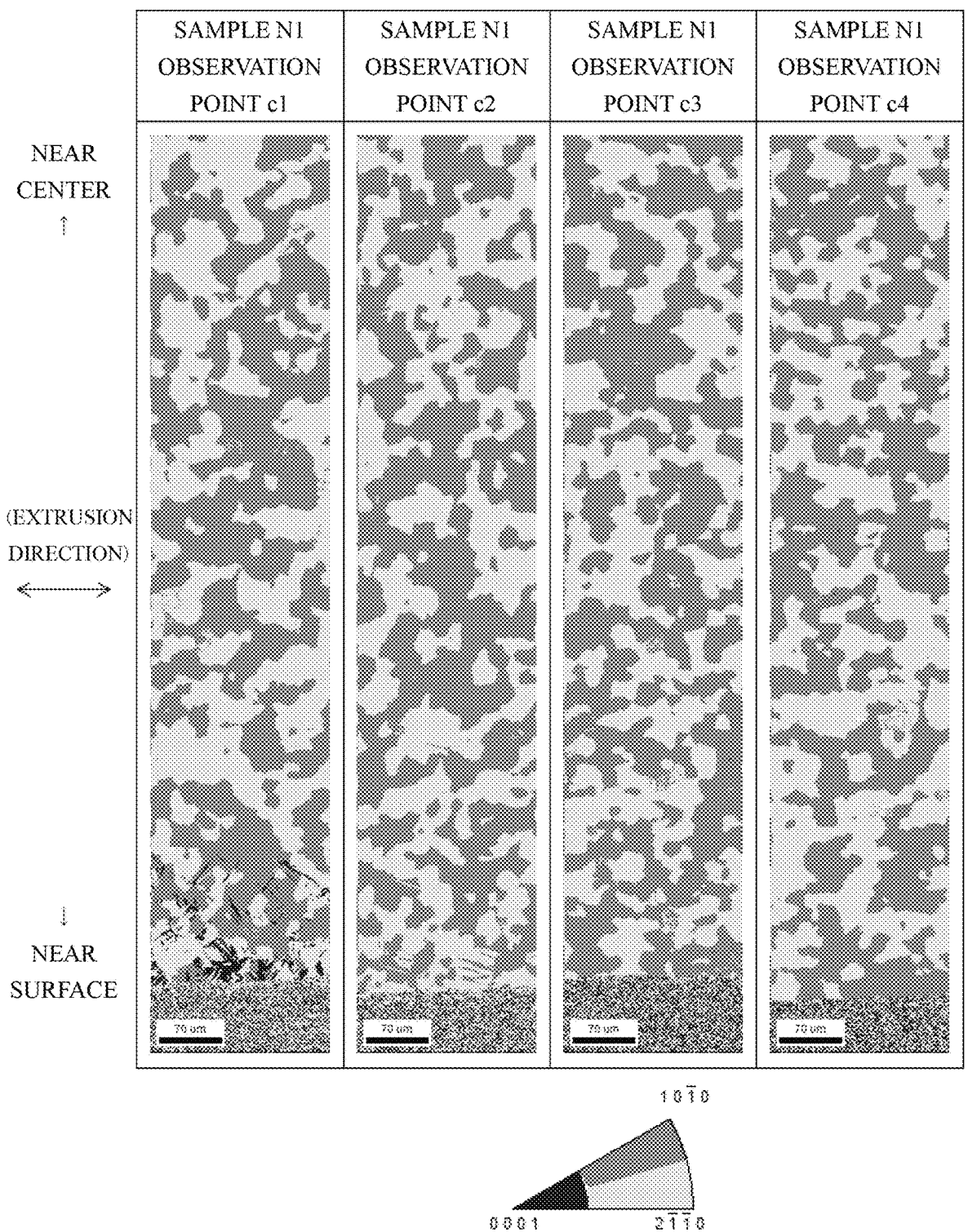
FIG. 18 is a diagram illustrating the orientation of the magnesium crystal grains when the observation points c1 to c4 in the longitudinal section of (Sample N1) are observed from the axis 2 direction.

FIG. 16 to FIG. 18 show the orientation of the magnesium crystal grains when the observation points c1 to c4 in the longitudinal section of (Sample N1) are observed from the axis 3 direction, the axis 1 direction, and the axis 2 direction, respectively. According to FIG. 16 to FIG. 18, it is found that the orientation of the magnesium crystal grains at the points separated in the longitudinal direction in the longitudinal section of (Sample N1) is substantially the same along most of its longitudinal direction.

Figure 19:
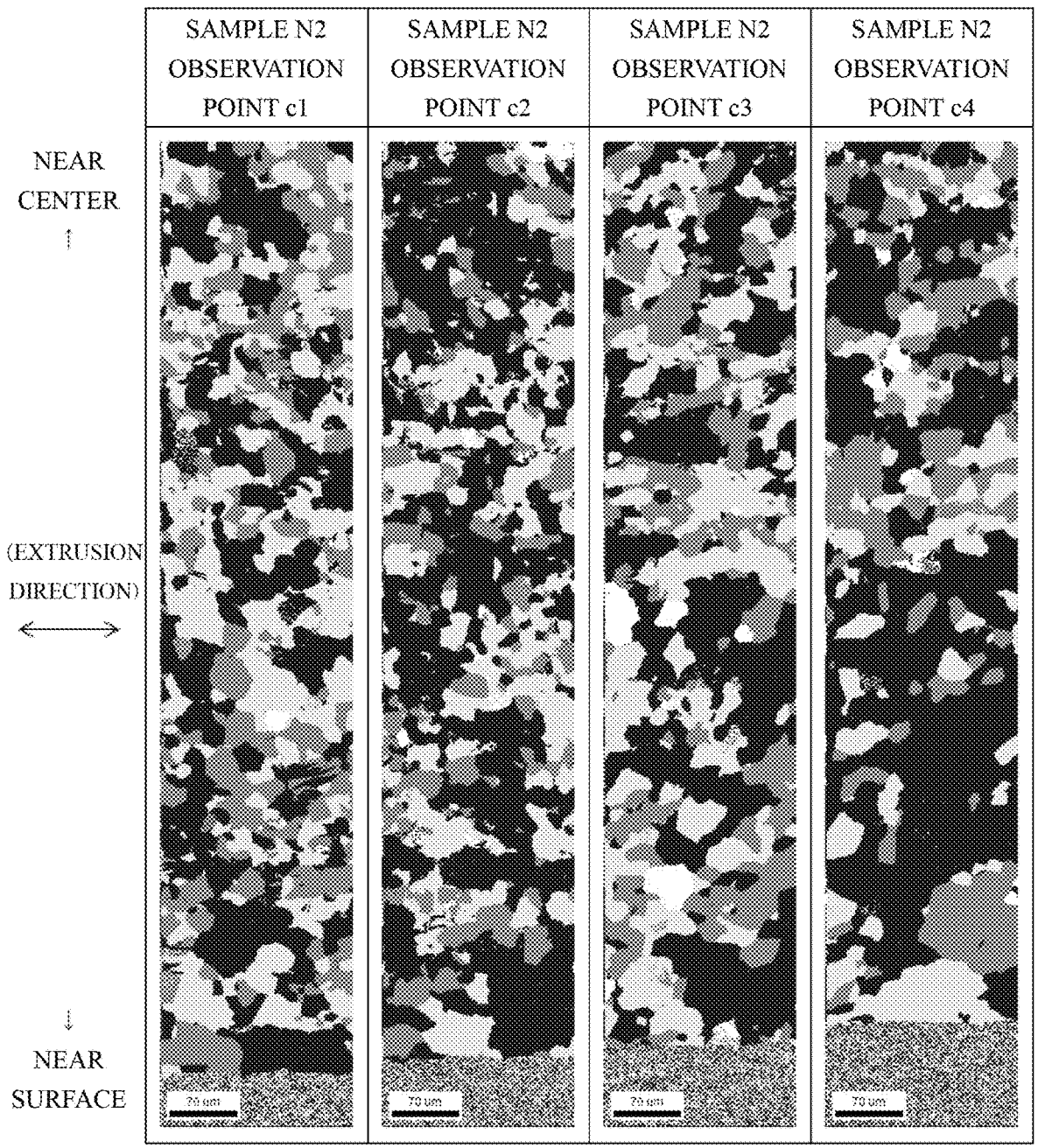
FIG. 19 is a diagram illustrating the orientation of the magnesium crystal grains when the observation points c1 to c4 in the longitudinal section of (Sample N2) are observed from the axis 3 direction.
Figure 19:
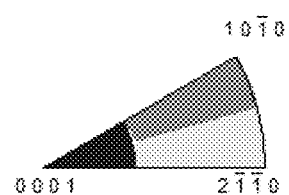
Figure 20:
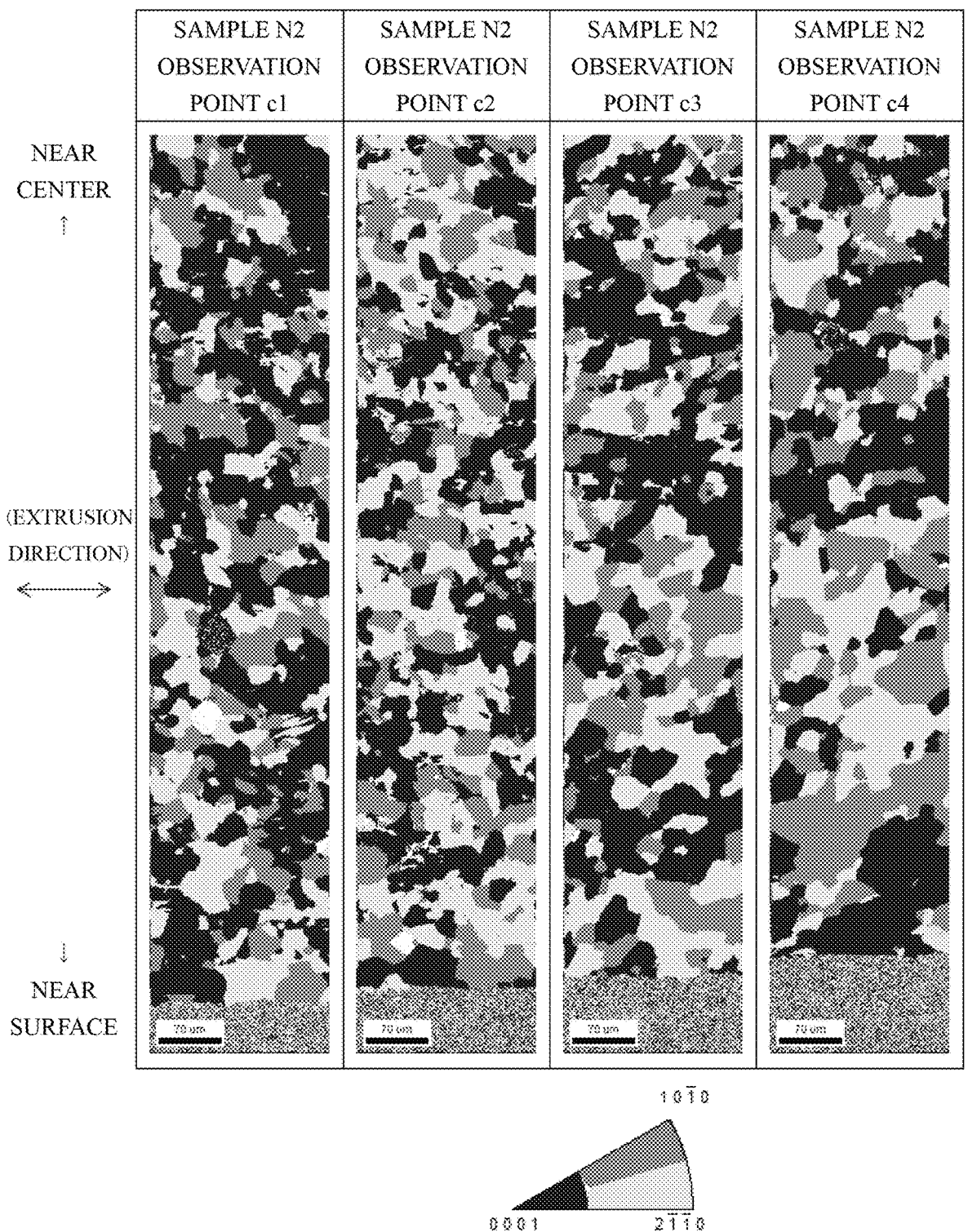
FIG. 20 is a diagram illustrating the orientation of the magnesium crystal grains when the observation points c1 to c4 in the longitudinal section of (Sample N2) are observed from the axis 1 direction.
Figure 21:
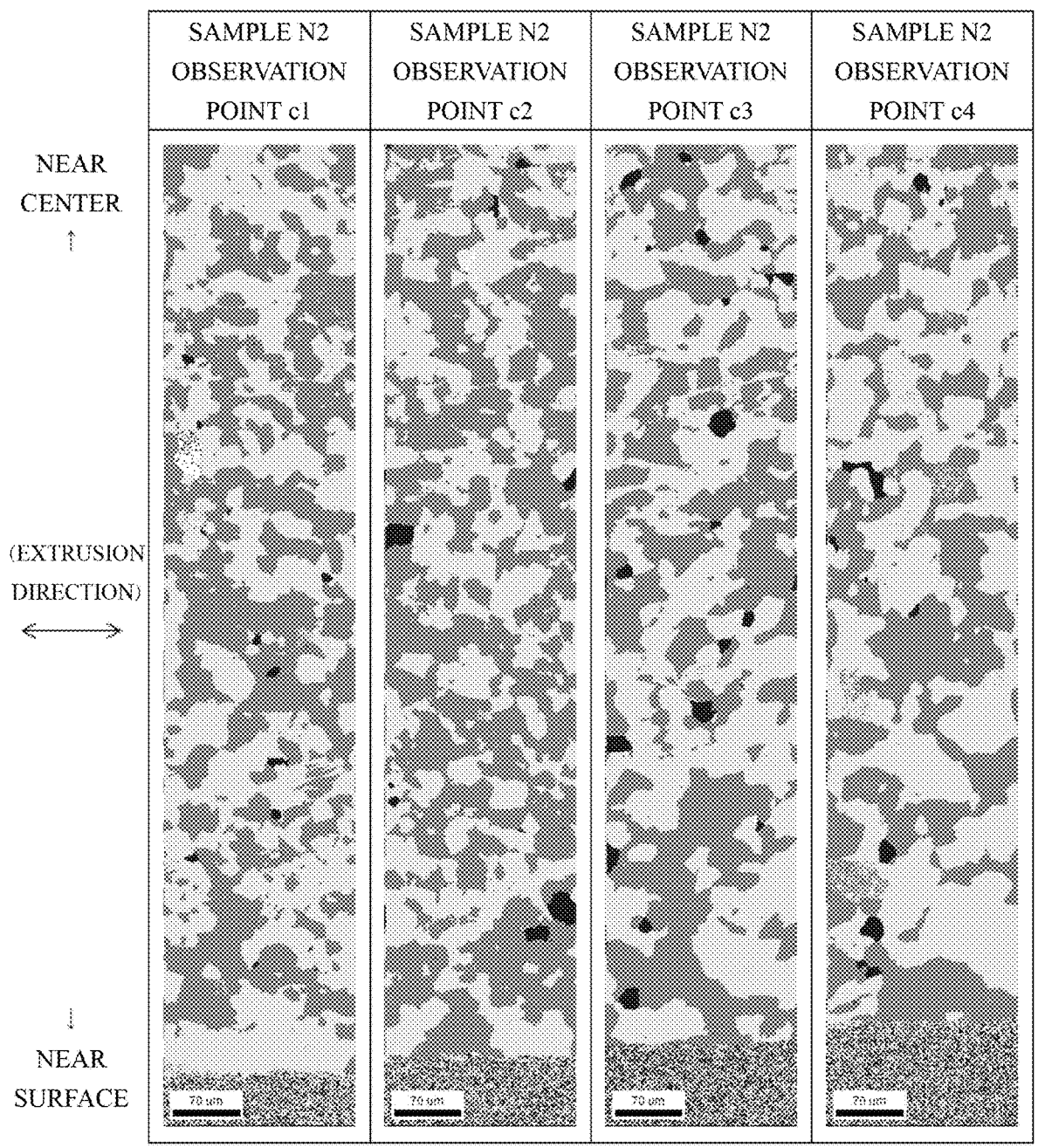
FIG. 21 is a diagram illustrating the orientation of the magnesium crystal grains when the observation points c1 to c4 in the longitudinal section of (Sample N2) are observed from the axis 2 direction.
Figure 21:
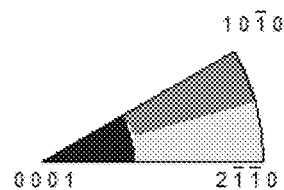

FIG. 19 to FIG. 21 show the orientation of the magnesium crystal grains when the observation points c1 to c4 in the longitudinal section of (Sample N2) are observed from the axis 3 direction, the axis 1 direction, and the axis 2 direction, respectively. According to FIG. 19 to FIG. 21, it is found that, like (Sample N1), the orientation of the magnesium, crystal grains at the two points separated in the longitudinal direction on the surface of (Sample N2) is substantially the same along most of its longitudinal direction.

Specifically, according to FIG. 16 and FIG. 19, it is found that the crystal grains shown in black color, the crystal grains shown in dark gray color, and the crystal grains shown in light gray color are mixed over the entire area from near the surface of the sample to near the center. According to FIG. 17 and FIG. 20, it is found that there are more crystal grains shown in black color near the surface of the sample than near the center of the sample. According to FIG. 18 and FIG. 21, it is found that there are almost no crystal grains shown in black color.

(Distribution of Crystal Grains)

The distribution of the crystal grains in which the (0001) plane in the hexagonal crystal structure is oriented toward the surface side has a large effect on the corrosion resistance (dissolubility) of the sample. Thus, the orientation of the magnesium crystal grains of (Sample N1) and (Sample N2) is examined in detail when the outer peripheral surface of the sample is observed from the outside in a direction perpendicular to the outer peripheral surface (axis 1 direction).

(Distribution of Crystal Grains in Transverse Section)

Transverse Section of (Sample N1)

Figure 22:
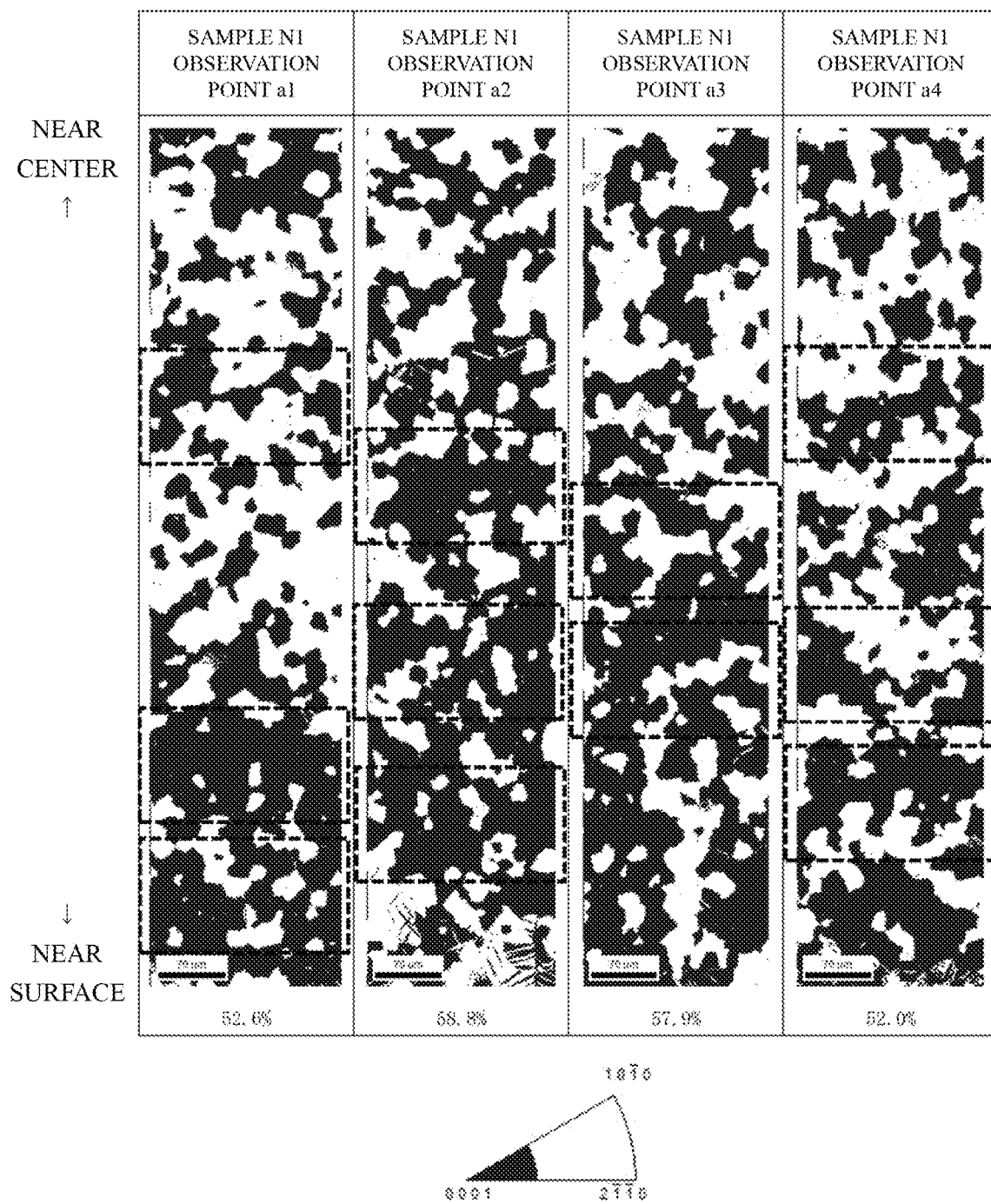
FIG. 22 is a diagram illustrating distribution of layers of magnesium crystal grains in which a (0001 plane) in a hexagonal crystal structure is oriented toward a surface side when the observation points a1 to a4 in the transverse section of (Sample N1) are each observed from the axis 1 direction.

FIG. 22 shows, in black color, the distribution of the crystal grains in which the (0001) plane in the hexagonal crystal structure is oriented toward the surface side of the sample when the observation points a1 to a4 in the transverse section of (sample N1) are each observed from the axis 1 direction. Note that FIG. 22 is the same as FIG. 11 except that only the magnesium crystal grains in black color are shown.

As described above, the observation points a1 to a4 are points separated from each other by 90 degrees in the circumferential direction (a direction around the axis of the sample) on the surface of the sample in the transverse section, and the let-right direction in FIG. 22 corresponds to the circumferential direction of the sample. Note that the same applies to FIG. 24.

In the distributions at the observation points a1 to a4, it is found that, for example, in each of regions surrounded by dotted lines, the crystal grains shown in black color are continuously distributed over the entire area in the left-right direction. Note that, in the present embodiment, a part where the crystal grains shown in black color are continuous in FIG. 22 is referred to as a layer of crystal grains in which the (0001 plane) in the hexagonal crystal structure is oriented toward the surface side of the sample. This point is the same for FIG. 24 to FIG. 26. In this manner, any of the observation points a1 to a4 in FIG. 22 include at least one region where the layer of crystal grains in which the (0001 plane) is oriented toward the surface side of the sample is continuously distributed over the entire area in the circumference direction of the sample.

Figure 23:
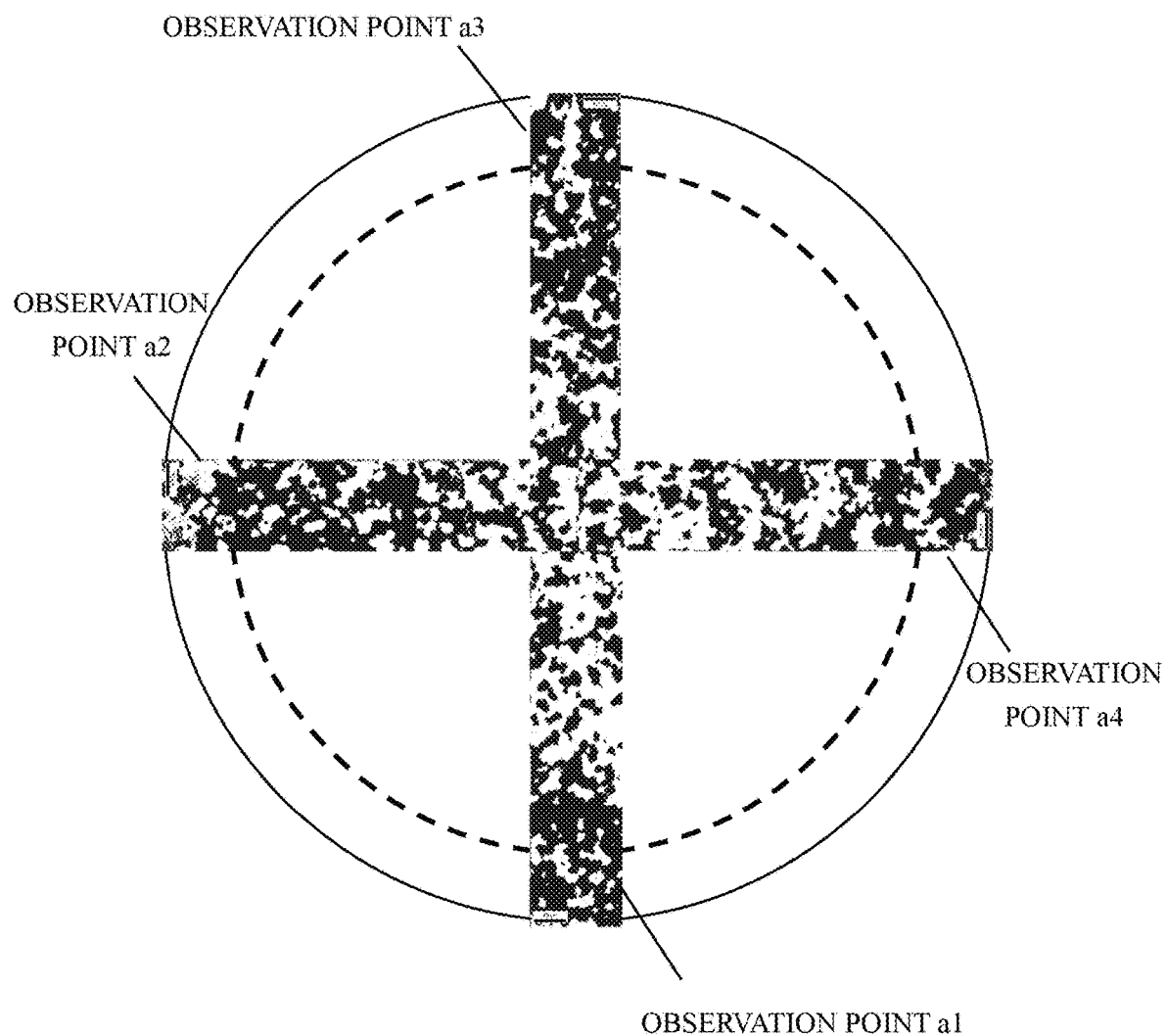
FIG. 23 is a diagram illustrating the distribution of the layers of magnesium crystal grains in which the (0001 plane) in the hexagonal crystal structure is oriented toward the surface side when the transverse section of (Sample N1) is observed from the axis 1 direction.

FIG. 23 is a diagram in which the distribution of the observation points a1 to a4 in FIG. 22 is arranged so as to correspond to the transverse section. The layer of crystal grains in which the (0001 plane) in the hexagonal crystal structure is oriented toward the surface side of the sample is continuously distributed over the entire area along the circumferential direction of the sample at each of the observation points a1 to a4, which are separated from each other by 90 degrees in the circumferential direction on the surface of the sample.

It is thought, upon observation of a region of a predetermined width (a length around the axis of the sample) extending from the sample surface to the center portion in a place other than the four observation points a1 to a4 in the circumferential direction (a region indicated by a dotted line in FIG. 23) in the transverse section, like the observation points a1 to a4, the observed region includes at least one region where the layer of crystal grains in which the (0001 plane) is oriented toward the surface side of the sample is continuously distributed over the entire area in the circumference direction of the sample. That is, it is thought that, in transverse section of the sample, a straight line connecting any position on the surface of the sample with the center portion of the sample passes through at least one layer of crystal grains in which the (0001 plane) is oriented toward the surface side of the sample.

Further, in the transverse section of the sample, the layer of crystal grains in which the 0001 plane is oriented toward the surface side of the sample continuously extends from the surface side of the sample to the center side, thereby connecting the layers of crystal grains adjacent to each other in the circumferential or radial direction of the sample. As a result, especially on the side near the surface of the sample (a part where the stress seems to be applied during cutting or drawing), a structure is formed in which the layers of crystal grains with the 0001 planes oriented toward the surface side of the sample are partially connected in a mesh pattern.

Thus, in the transverse section of (sample N1), the layer of magnesium crystal grains in which the (0001 plane) in the hexagonal crystal structure is oriented toward the surface side of the sample is continuous over the entire circumference. That is, the layer of magnesium crystal grains surrounds the center portion of the biodegradable medical implement.

Transverse Section of (Sample N2)

Figure 24:
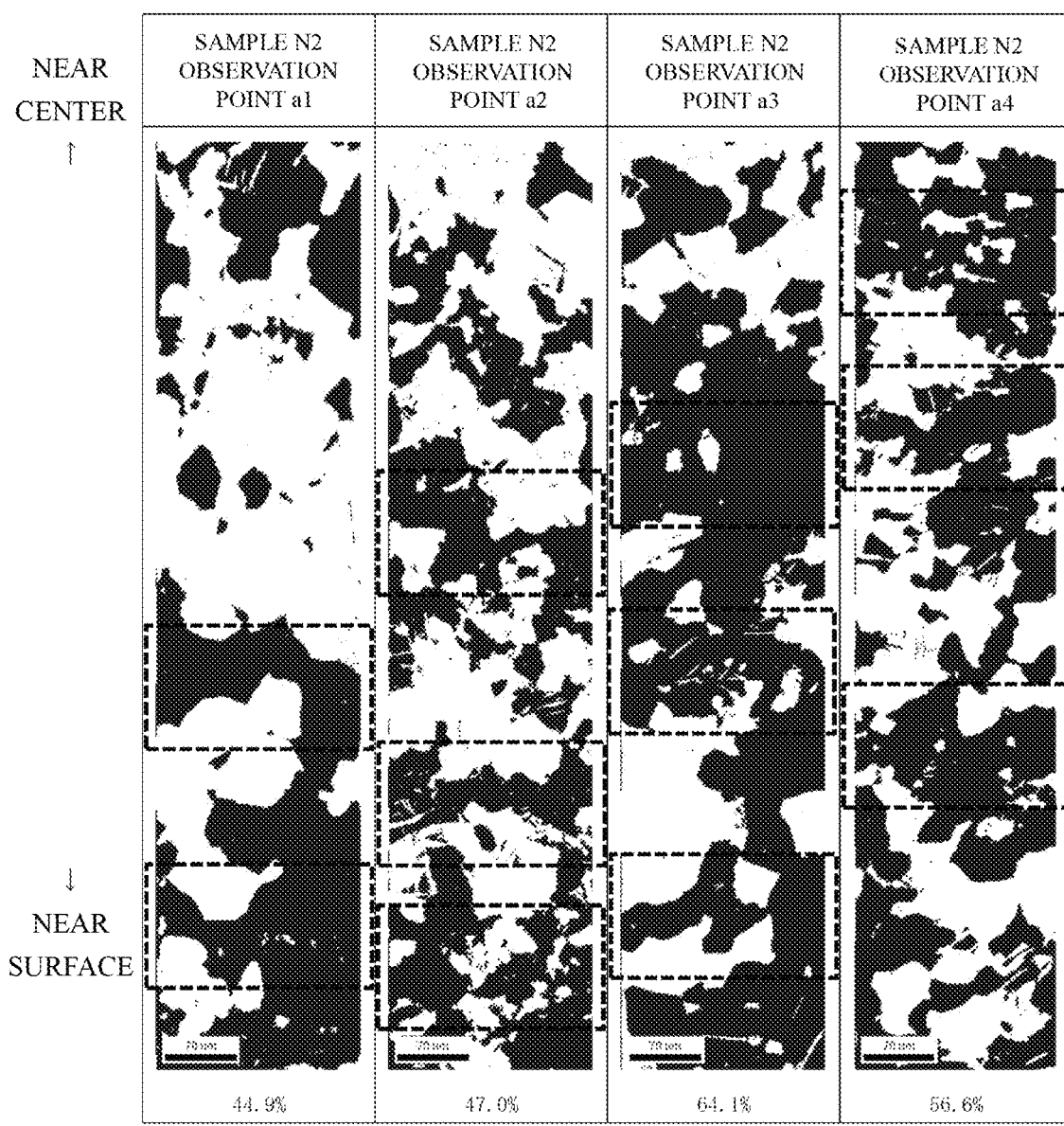
FIG. 24 is a diagram illustrating the distribution of the layers of magnesium crystal grains in which the (0001 plane) in the hexagonal crystal structure is oriented toward the surface side when the observation points a1 to a4 in the transverse section of (Sample N2) are each observed from the axis 1 direction.

FIG. 24 shows, in black color, the distribution of the crystal grains in which the (0001) plane in the hexagonal crystal structure is oriented toward the surface side of the sample when the observation points a1 to a4 in the transverse section of (sample N2) are each observed from the axis 1 direction. Note that FIG. 24 is the same as FIG. 14 except that only the magnesium crystal grains in black color are shown.

In the distribution at the observation points a1 to a4, it is found that, for example, in each of regions surrounded by dotted lines, the crystal grains shown in black color are continuously distributed over the entire area in the left-right direction. In this manner, any of the observation points a1 to a4 in FIG. 24 include at least one region where the layer of crystal grains in which the (0001 plane) is oriented toward the surface side of the sample is continuously distributed over the entire area in the circumference direction of the sample.

Thus, like the transverse section of (sample N1), in the transverse section of (sample N2), the layer of magnesium crystal grains in which the (0001 plane) in the hexagonal crystal structure is oriented toward the surface side of the sample is continuous over the entire circumference. That is, the layer of magnesium crystal grains surrounds the center portion of the biodegradable medical implement.

(Distribution of Crystal Grains in Longitudinal Section)

Longitudinal Section of (Sample N1)

Figure 25:
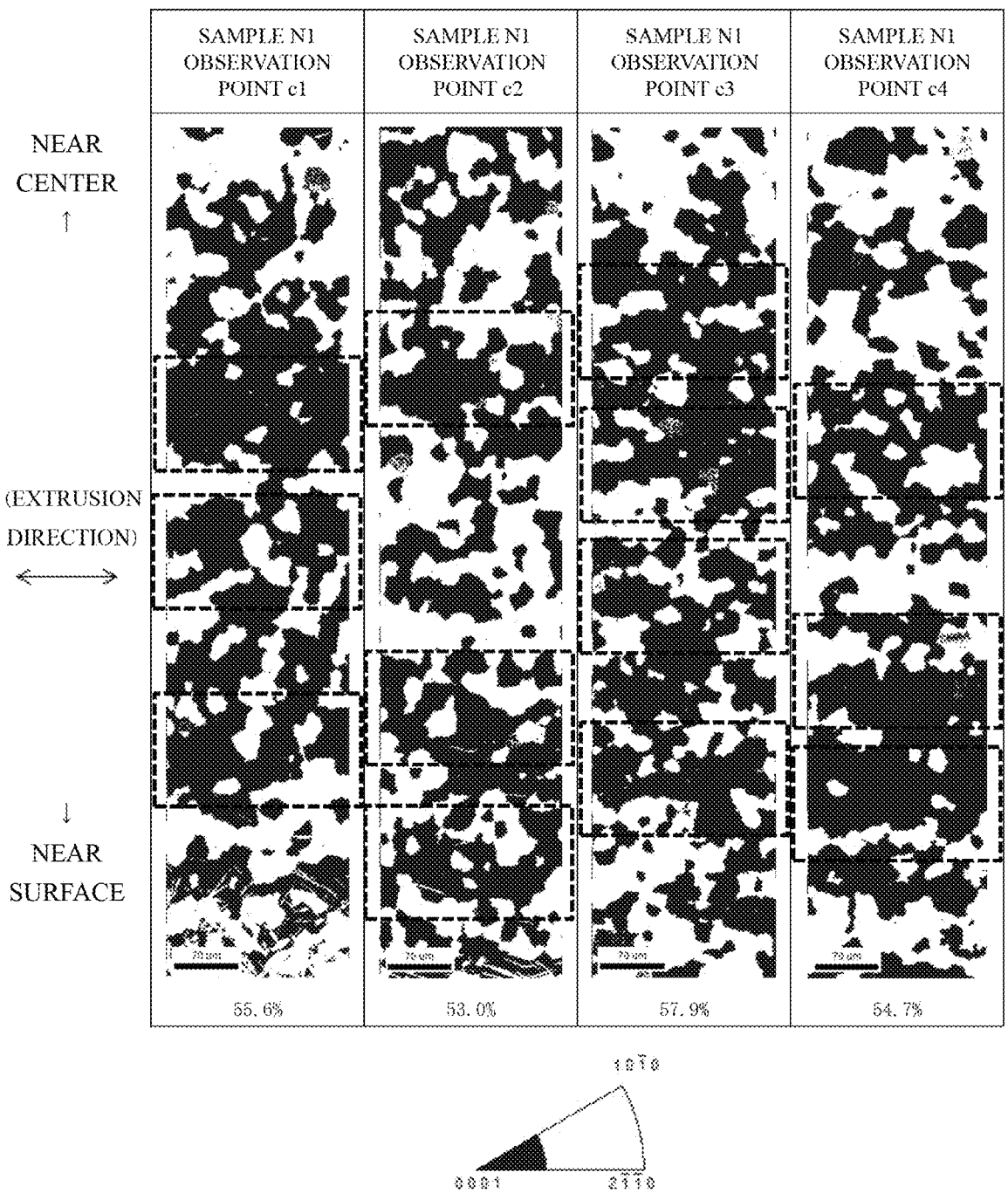
FIG. 25 is a diagram illustrating the distribution of the layers of magnesium crystal grains in which the (0001 plane) in the hexagonal crystal structure is oriented toward the surface side when the observation points c1 to c4 in the longitudinal section of (Sample N1) are each observed from the axis 1 direction.

FIG. 25 shows, in black color, the distribution of the crystal grains in which the (0001) plane in the hexagonal crystal structure is oriented toward the surface side of the sample when the observation points c1 to c4 in the longitudinal section of (sample N1) are each observed from the axis 1 direction. Note that FIG. 25 is the same as FIG. 17 except that only the magnesium crystal grains in black color are shown.

As described above, the observation points c1 to c4 are points separated in the longitudinal direction in the longitudinal section of the sample, and the left-right direction in FIG. 25 corresponds to the longitudinal direction of the sample. Note that the same applies to FIG. 26.

In the distribution at the observation points c1 to c4, it is found that, for example, in regions surrounded by dotted lines, the crystal grains shown in black color are continuously distributed over the entire area in the left-right direction. In this manner, any of the observation points c1 to c4 in FIG. 25 include at least one region where the layer of crystal grains in which the (0001 plane) in the hexagonal crystal structure is oriented toward the surface side of the sample is continuously distributed over the entire area in the longitudinal direction of the sample.

It is thought that, upon observation of a region of a predetermined width (a length along the longitudinal direction of the sample) extending from the sample surface to the center portion in a place other than the four observation points c1 to c4 in the longitudinal direction in the longitudinal section, like the observation points c1 to c4, the observed region includes at least one region where the layer of crystal grains in which the (0001 plane) is oriented toward the surface side of the sample is continuously distributed over the entire area in the longitudinal direction of the sample.

Further, in the longitudinal section of the sample, the layer of crystal grains in which the 0001 plane is oriented toward the surface side of the sample continuously extends from the surface side of the sample to the center side, thereby connecting the layers of crystal grains adjacent to each other in the longitudinal or radial direction of the sample. As a result, especially on the side near the surface of the sample (a part where the stress seems to be applied during cutting or drawing), a structure is formed in which the layers of crystal grains with the 0001 planes oriented toward the surface side of the sample are partially connected in a mesh pattern.

Thus, in the longitudinal section of (sample N1), the layer of crystal grains in which the (0001 plane) in the hexagonal crystal structure is oriented toward the surface side of the sample is continuously distributed in the longitudinal direction between the two observation points c1 and c2 and between the two observation points c3 and c4.

Longitudinal Section of (Sample N2)

Figure 26:
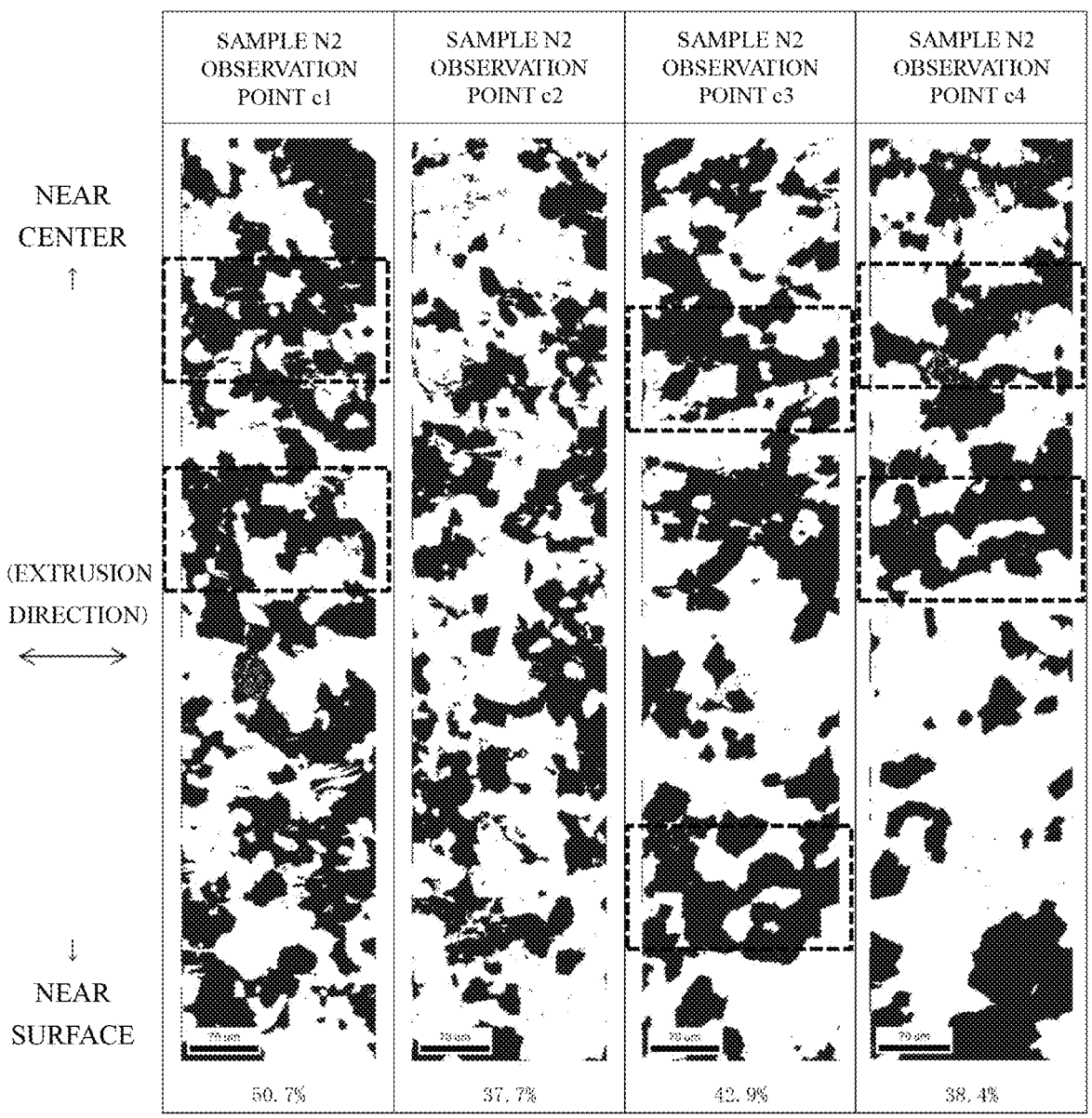
FIG. 26 is a diagram illustrating the distribution of the layers of magnesium crystal grains in which the (0001 plane) in the hexagonal crystal structure is oriented toward the surface side when the observation points c1 to c4 in the longitudinal section of (Sample N2) are each observed from the axis 1 direction.
Figure 26:
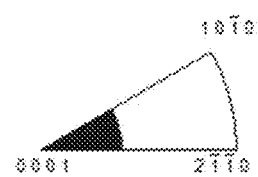

FIG. 26 shows, in black color, the distribution of the crystal grains in which the (0001) plane in the hexagonal crystal structure is oriented toward the surface side of the sample when the observation points c1 to c4 in the longitudinal section of (sample N2) are each observed from the axis 1 direction. Note that FIG. 26 is the same as FIG. 20 except that only the magnesium crystal grains in black color are shown.

In the distribution at the observation points c1, c3, and c4 in FIG. 26, it is found that, for example, in regions surrounded by dotted lines, the crystal grains shown in black color are continuously distributed over the entire area in the left-right direction. In this manner, any of the observation points c1 to c4 in FIG. 26 include at least one region where the layer of crystal grains in which the (0001 plane) in the hexagonal crystal structure is oriented toward the surface side of the sample is continuously distributed over the entire area in the longitudinal direction of the sample.

On the other hand, in the distribution at the observation point c2, it is found that the crystal grains shown in black color are not continuously distributed over the entire area in the left-right direction. In this manner, the observation point c2 in FIG. 26 does not include the region where the layer of crystal grains in which the (0001 plane) in the hexagonal crystal structure is oriented toward the surface side of the sample is continuously distributed over the entire area in the longitudinal direction of the sample.

Figure 27A:
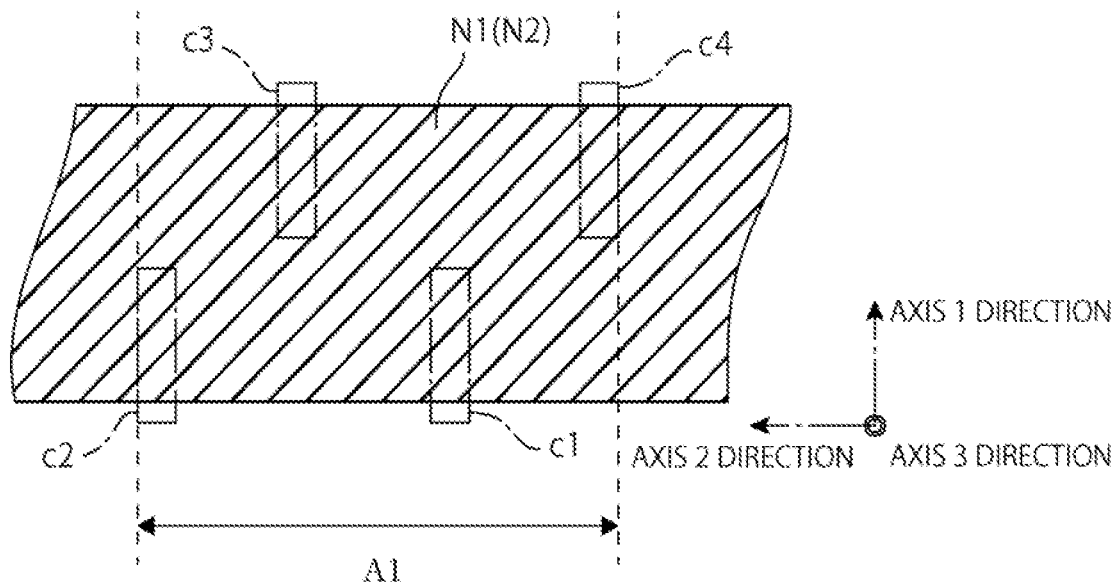
FIG. 27A and FIG. 27B are diagrams explaining a range in which the layers of magnesium crystal grains are continuous in a longitudinal direction.

As described above, it is thought that, in the longitudinal section of (Sample N1), the layer of magnesium crystal grains in which the (0001 plane) in the hexagonal crystal structure is oriented toward the surface side of the sample is continuous at least in a range A1 of the observation points c2 to c4 as shown in FIG. 27A.

Figure 27B:
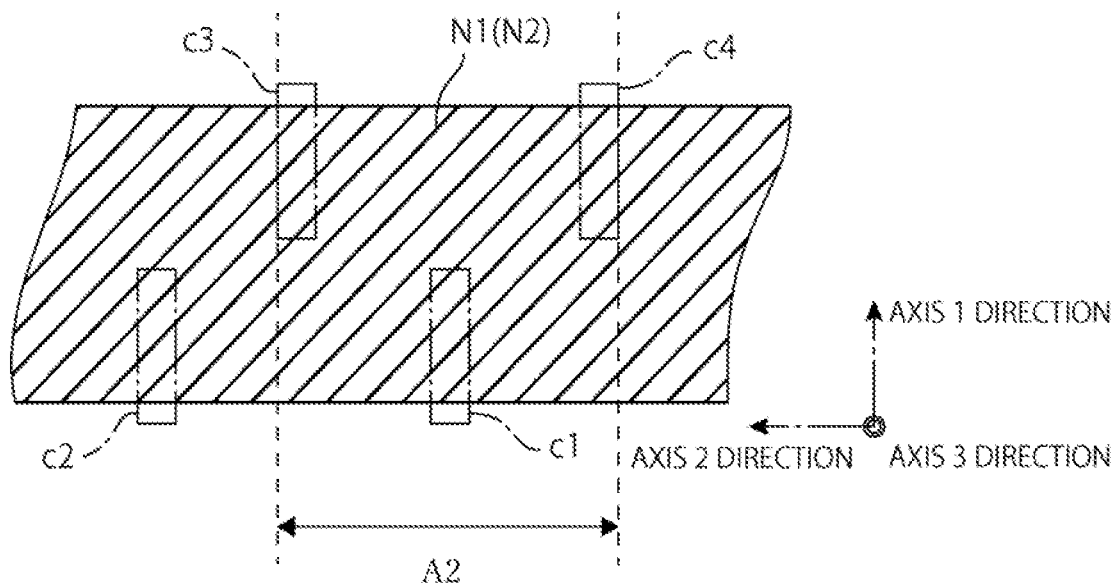

On the other hand, it is thought that, in the longitudinal section of (Sample N2), the layer of magnesium crystal grains in which the (0001 plane) in the hexagonal crystal structure is oriented toward the surface side of the sample is continuous at least in a range A2 of the observation points c3 to c4 as shown in FIG. 27B.

Thus, it is thought that the range in which the layer of magnesium crystal grains in which the (0001 plane) in the hexagonal crystal structure is oriented toward the surface side of the sample is continuous in the longitudinal direction is larger in (Sample N1) than (Sample N2).

(Dissolubility Evaluation Test)

(Sample N1) and (Sample N2) were subjected to a dissolubility evaluation test. In the dissolubility evaluation test, the sample was immersed in a simulated body fluid prepared by adding sodium bicarbonate [manufactured by FUJIFILM Wako Pure Chemical Corp.: product number 199-05985] to HBSS (+) [manufactured by FUJIFILM Wako Pure Chemical Corp.: product number 082-08961] for adjusting pH to 7.67, and a weight change of the sample was measured. The container in which the sample was immersed was placed in a multi-gas incubator [manufactured by Panasonic Healthcare: model MCO-170MUVH-PJ] and maintained at an internal temperature of 37 degrees and a $CO^2$ concentration of 5%.

Figure 28:
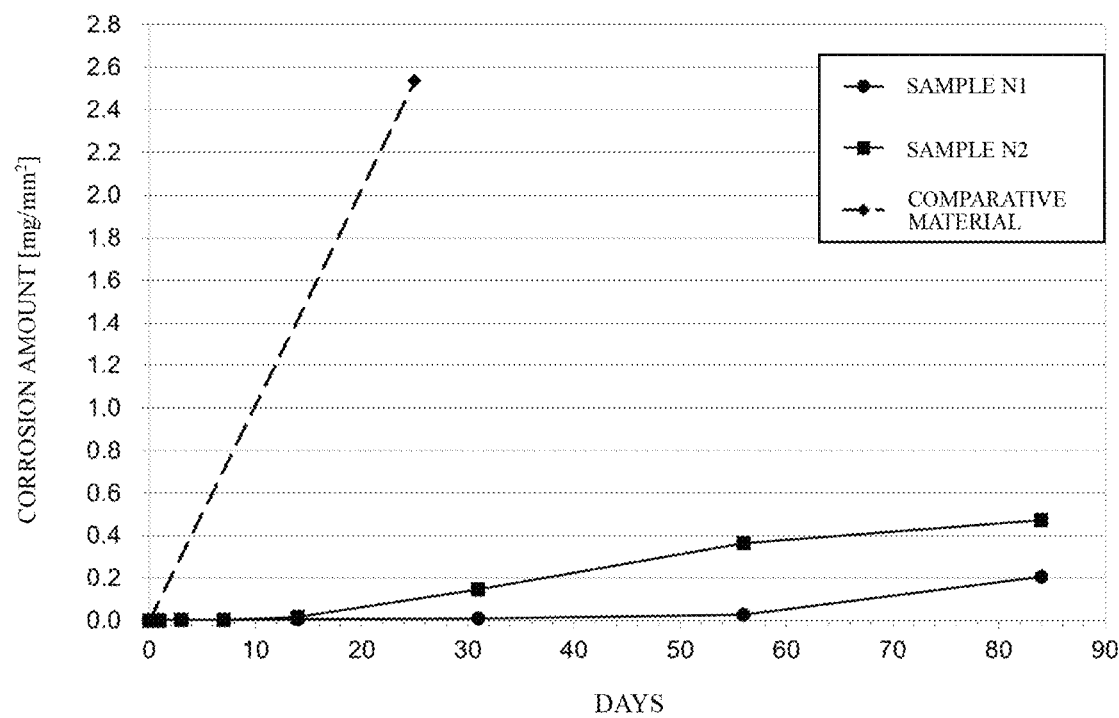
FIG. 28 is a diagram showing data obtained from a dissolubility evaluation test.

FIG. 28 shows data obtained from the dissolubility evaluation test for (Sample N1) and (Sample N2). Note that the horizontal axis in FIG. 28 indicates the number of days from the start of the dissolubility evaluation test, and the vertical axis indicates the amount of corrosion of the sample (the weight of the sample that is decreased due to dissolution).

According to FIG. 28, it is found that (Sample N1) had almost no change in weight until about 56 days after the start of immersion, and the weight gradually decreased after about 56 days. On the other hand, it is found that (Sample N2) had almost no change in weight until about 10 days after the start of immersion, and the weight gradually decreased after about 10 days.

Note that FIG. 28 includes data obtained from the dissolubility evaluation test for a comparative material for comparison with the dissolubility of (Sample N1) and (Sample N2). In the dissolubility evaluation test for the comparative material, the comparative material was immersed in a simulated body fluid containing only HBSS (+), and the container in which the sample was immersed was maintained at an internal temperature of 37 degrees.

As the comparative material, an extruded material formed of a pure magnesium material containing 99.9% by mass or more of magnesium and obtained by extrusion molding was used. The dimensions of samples N1 and N2 and the comparative material used in the dissolubility evaluation test are as follows.

Samples N1 and N2: ϕ2×50 mm(volume 157 mm³)

Comparative material: ϕ7.7×12 mm(volume 558.5 mm³)

As described above, (Sample N1) and (Sample N2) are obtained by cutting or drawing the extruded material obtained by extrusion molding, while the comparative material is the extruded material obtained by extrusion molding without cutting or drawing. The graph of the comparative material in FIG. 28 shows that all of the comparative material dissolved and disappeared after about 25 days from the start of immersion.

In both (Sample N1) and (Sample N2), at least in one transverse section, the layer of magnesium crystal grains in which the (0001 plane) in the hexagonal crystal structure is oriented toward the surface side of the sample is continuous over the entire circumference. Thus, as shown in FIG. 28, it is found that the dissolution rates of (Sample N1) and (Sample N2) are very slow compared with the dissolution rate of the comparative material.

Note that different simulated body fluids were used in the dissolubility evaluation test for (Sample N1) and (Sample N2) and the dissolubility evaluation test for the comparative material. However, when the simulated body fluid contains only HBSS (+) as in the dissolubility evaluation test for the comparative material, the pH is higher (more alkaline) than the simulated body fluid obtained by adding sodium bicarbonate to HBSS (+) as in the dissolubility evaluation test for (Sample N1) and (Sample N2). Thus, the simulated body fluid containing only HBSS (+) has a property which makes the pure magnesium less dissolvable. That is, despite the test environment in which the comparative material is less dissolvable than (Sample N1) and (Sample N2), the result shows that the comparative material dissolves and disappears earlier. Further, although the volume of the comparative material is larger than that of (Sample N1) and (Sample N2), the result shows that the comparative material dissolves and disappears earlier.

Further, it is found that the transverse section in which the layer of magnesium crystal grains described above is continuous over the entire circumference is continuous in a wider range in the longitudinal direction in (Sample N1) than in (Sample N2), resulting in that the dissolution rate of (Sample N1) is further slower than that of (Sample N2).

Note that, in the present embodiment, according to the result of detecting the orientation of the magnesium crystal grains by the electron back-scatter diffraction method, it is found that the orientation of the crystal grains can be well-oriented over the entire circumference by subjecting the extruded material obtained by extrusion molding to processing which can apply uniform stress from the entire outer periphery to the inside, such as drawing, cutting, or pressing.

As described above, the biodegradable medical implement of the present embodiment is formed of the magnesium material, and, at least in one transverse section, the layer of magnesium crystal grains in which the (0001) plane in the hexagonal crystal structure is oriented toward the surface side is continuous over the entire circumference.

As a result, in the biodegradable medical implement of the present embodiment, in the transverse section, the layer of magnesium crystal grains in which the (0001) plane, which has higher corrosion resistance in vivo than the (10-10) plane and the (2-1-10) plane in the hexagonal crystal structure, is oriented toward the surface side is continuous over the entire circumference. Thus, dissolution hardly progresses from the surface of the biodegradable medical implement toward the center portion of the implement from any direction in the circumferential direction. Thus, the progress of dissolution from the surface of the biodegradable medical implement toward the center portion of the implement is delayed as compared with the case where the magnesium crystal grains in which the (10-10) plane or the (2-1-10) plane with low in vivo corrosion resistance is oriented toward the surface side are present at least in a part of the surface of the biodegradable medical implement. This can improve the corrosion resistance of the biodegradable medical implement to make the biodegradable medical implement hardly dissolvable.

In the biodegradable medical implement of the present embodiment, the layer of magnesium crystal grains is continuous in the direction perpendicular to the transverse section.

As a result, in the biodegradable medical implement of the present embodiment, in the transverse section, the layer of magnesium crystal grains, in which the dissolution hardly progresses from the surface of the biodegradable medical implement toward the center portion of the implement from any direction in the circumferential direction in the transverse section, is continuous in the longitudinal direction. This can further improve the corrosion resistance of the biodegradable medical implement to make the biodegradable medical implement hardly dissolvable.

In the biodegradable medical implement of the present embodiment, the magnesium material is a pure magnesium material containing 99.9% by mass or more of magnesium.

As a result, in the biodegradable medical implement of the present embodiment, even when a high-purity magnesium material having low corrosion resistance in vivo is used as the magnesium material, the corrosion resistance of the biodegradable medical implement can be improved to make the biodegradable medical implement hardly dissolvable.

The embodiment of the present invention has been described above. However, the configuration of the present embodiment is not limited to the above, and various modifications can be made.

For example, in the above embodiment, the plate, the pin, and the screw, which are used, for example, for attaching or fixing bones in the body, have been described as the biodegradable medical implement. However, the biodegradable medical implement is not limited to these. Any shape and use method of the biodegradable medical implement may be adopted. In the above embodiment, the cylindrical sample has been described as the biodegradable medical implement. However, the effects of the present invention can be obtained regardless of the shape of the biodegradable medical implement.

In the above embodiment, the biodegradable medical implement is formed of a pure magnesium material containing 99.9% by mass or more of magnesium without being limited thereto. The biodegradable medical implement may be formed of a magnesium alloy containing magnesium as a main component. For example, the magnesium alloy of the present invention contains, by mass %, 1.0 to 2.0% Zn, 0.05 to 0.80% Zr, and 0.05 to 0.40% Mn, with the balance being Mg and unavoidable impurities. Further, the magnesium alloy of the present invention may further contain Ca in an amount of 0.005% or more and less than 0.20% by mass %. That is, the magnesium alloy may contain, by mass %, 1.0 to 2.0% Zn, 0.05 to 0.80% Zr, 0.05 to 0.40% Mn, and 0.005% or more and less than 0.20% Ca, with the balance being Mg and unavoidable impurities. Even in that case, the same effects as in the above embodiment can be obtained.

Other configurations can also be modified in various ways without departing from the gist of the present invention.

INDUSTRIAL APPLICABILITY

The present invention can be used, for example, as a biodegradable medical implement that dissolves in vivo.

The invention claimed is:
1. A biodegradable medical implement, wherein:
the biodegradable medical implement is cylindrical and formed of a magnesium material;
the biodegradable medical implement comprises a side surface;

at least in one predetermined cross section perpendicular to a longitudinal direction, a layer of magnesium crystal grains in which a (0001) plane in a hexagonal crystal structure is oriented toward the surface side is continuous over an entire circumference; and the medical implement comprises a solid cylinder.

2. The biodegradable medical implement according to claim 1, wherein the layer of magnesium crystal grains has a structure in which a portion of the layer is connected in a mesh pattern.

3. The biodegradable medical implement according to claim 1, wherein the layer of magnesium crystal grains is continuous in a direction perpendicular to the predetermined cross section.

4. The biodegradable medical implement according to claim 2, wherein the layer of magnesium crystal grains is continuous in a direction perpendicular to the predetermined cross section.

5. The biodegradable medical implement according to claim 1, wherein the magnesium material is a pure magnesium material containing 99.9% by mass or more of magnesium.

6. The biodegradable medical implement according to claim 2, wherein the magnesium material is a pure magnesium material containing 99.9% by mass or more of magnesium.

7. The biodegradable medical implement according to claim 3, wherein the magnesium material is a pure magnesium material containing 99.9% by mass or more of magnesium.

8. The biodegradable medical implement according to claim 4, wherein the magnesium material is a pure magnesium material containing 99.9% by mass or more of magnesium.

9. The biodegradable medical implement according to claim 1, wherein the magnesium material is a magnesium alloy containing magnesium as a main component.

10. The biodegradable medical implement according to claim 2, wherein the magnesium material is a magnesium alloy containing magnesium as a main component.

11. The biodegradable medical implement according to claim 3, wherein the magnesium material is a magnesium alloy containing magnesium as a main component.

12. The biodegradable medical implement according to claim 4, wherein the magnesium material is a magnesium alloy containing magnesium as a main component.

* * * * *

UNITED STATES PATENT AND TRADEMARK OFFICE
CERTIFICATE OF CORRECTION

PATENT NO. : 12,029,450 B2
APPLICATION NO. : 18/266639
DATED : July 9, 2024
INVENTOR(S) : Masakazu Ishihara et al.

It is certified that error appears in the above-identified patent and that said Letters Patent is hereby corrected as shown below:

On the Title Page

(71) Applicants: NITTO SEIKO CO.,LTD., Ayabe (JP);
KYOTO PREFECTURAL PUBLIC UNIVERSITY CORPORATION, Kyoto-shi(JP);
Wook-Cheol Kim, Kyoto(JP);
NATIONAL UNIVERSITY CORPORATION UNIVERSITY OF TOYAMA, Toyama(JP)
Should read:
(71) Applicants: NITTO SEIKO CO.,LTD., Ayabe (JP);
KYOTO PREFECTURAL PUBLIC UNIVERSITY CORPORATION, Kyoto-shi(JP);
Wook-Cheol Kim, Kyoto(JP);
NATIONAL UNIVERSITY CORPORATION UNIVERSITY OF TOYAMA, Toyama(JP)
Sadami Tsutsumi, Kyoto (JP)

Signed and Sealed this
Third Day of December, 2024

Katherine Kelly Vidal
*Director of the United States Patent and Trademark Office*